US005608526A

United States Patent [19]
Piwonka-Corle et al.

[11] Patent Number: 5,608,526
[45] Date of Patent: Mar. 4, 1997

[54] FOCUSED BEAM SPECTROSCOPIC ELLIPSOMETRY METHOD AND SYSTEM

[75] Inventors: Timothy R. Piwonka-Corle, Portland, Oreg.; Karen F. Scoffone, Redwood City, Calif.; Xing Chen, San Jose, Calif.; Lloyd J. Lacomb, Jr., Santa Clara, Calif.; Jean-Louis Stehle, Colombes, France; Dorian Zahorski, Vanves, France; Jean-Pierre Rey, Fontenay Aux Roses, France

[73] Assignee: Tencor Instruments, Santa Clara, Calif.

[21] Appl. No.: 375,353

[22] Filed: Jan. 19, 1995

[51] Int. Cl.$^6$ .................................................. G01N 21/21
[52] U.S. Cl. .................................................. 356/369
[58] Field of Search .................................. 356/364, 365, 356/366, 367, 369, 319, 328, 73

[56] References Cited

U.S. PATENT DOCUMENTS

| | | | |
|---|---|---|---|
| 4,210,401 | 7/1980 | Batten | 356/369 |
| 4,645,349 | 2/1987 | Tabata | 356/382 |
| 4,653,908 | 3/1987 | Yajima et al. | 356/51 |
| 4,653,924 | 3/1987 | Itonaga et al. | 356/369 |
| 4,655,595 | 4/1987 | Bjork et al. | 356/369 |
| 4,672,196 | 6/1987 | Canino | 250/225 |
| 4,790,659 | 12/1988 | Erman et al. | 356/369 |
| 4,834,539 | 5/1989 | Le Bris et al. | 356/369 |
| 4,865,445 | 9/1989 | Kuriyama et al. | 356/73 |
| 4,999,014 | 3/1991 | Gold et al. | 356/382 |
| 5,042,951 | 8/1991 | Gold et al. | 356/369 |
| 5,076,696 | 12/1991 | Cohn et al. | 356/369 |
| 5,096,298 | 3/1992 | Isobe | 356/369 |
| 5,159,412 | 10/1992 | Willenborg et al. | 356/445 |
| 5,166,752 | 11/1992 | Spanier et al. | 356/369 |
| 5,189,481 | 2/1993 | Jann et al. | 356/73 |
| 5,241,366 | 8/1993 | Bevis et al. | 356/382 |
| 5,251,007 | 10/1993 | Rinke | 356/319 |
| 5,329,357 | 7/1994 | Bernoux et al. | 356/369 |

*Primary Examiner*—Richard A. Rosenberger
*Attorney, Agent, or Firm*—Limbach & Limbach L.L.P.

[57] ABSTRACT

A method and system for spectroscopic ellipsometry employing reflective optics to measure a small region of a sample by reflecting radiation (preferably broadband UV, visible, and near infrared radiation) from the region. The system preferably has an autofocus assembly and a processor programmed to determine from the measurements the thickness and/or complex refractive index of a thin film on the sample. Preferably, only reflective optics are employed along the optical path between the polarizer and analyzer, a sample beam reflects with low incidence angle from each component of the reflective optics, the beam is reflectively focused to a small, compact spot on the sample at a range of high incidence angles, and an incidence angle selection element is provided for selecting for measurement only radiation reflected from the sample at a single, selected angle (or narrow range of angles). The focusing mirror preferably has an elliptical shape, to reduce off-axis aberrations in the focused beam. Some embodiments include both a spectrophotometer and an ellipsometer integrated together as a single instrument. In such instrument, the spectrophotometer and ellipsometer share a radiation source, and radiation from the source can be focused by either the spectrophotometer or the ellipsometer to the same focal point on a sample. Preferred embodiments of the ellipsometer employ a rotating, minimal-length Rochon prism as a polarizer, and include a spectrometer with an intensified photodiode array to measure reflected radiation from the sample, and a reference channel (in addition to a sample channel which detects radiation reflected from the sample).

72 Claims, 8 Drawing Sheets

FOCUSED BEAM SPECTROSCOPIC ELLIPSOMETRY METHOD AND SYSTEM

FIELD OF THE INVENTION

The invention relates to methods and systems for obtaining ellipsometric and reflectance measurements of a small region of a sample over a range of UV (and preferably also visible) wavelengths, and optionally also for determining, from the measurements, the thickness and refractive index of a very thin film on the sample. The sample can be a semiconductor wafer having at least one thin layer over a silicon substrate. Preferred embodiments of the invention include both a spectrophotometer and an improved spectroscopic ellipsometer which share a common focal point on the sample and preferably a common radiation source.

BACKGROUND OF THE INVENTION

Among the well known nondestructive testing techniques are the techniques of spectroreflectometry and spectroscopic ellipsometry, which measure reflectance data by reflecting electromagnetic radiation from a sample. In spectroscopic ellipsometry, an incident radiation beam having a known polarization state reflects from a sample (generally at high incidence angle), and the polarization of the reflected radiation is analyzed to determine properties of the sample. Since the incident radiation includes multiple frequency components, a spectrum of measured data (including data for incident radiation of each of at least two frequencies) can be measured. Typically, the polarization of the incident beam has a time-varying characteristic (produced, for example, by passing the incident beam through a mechanically rotating polarizer), and/or the means for analyzing the reflected radiation has a time-varying characteristic (for example, it may include a mechanically rotating analyzer). Examples of spectroscopic ellipsometry systems are described in U.S. Pat. No. 5,329,357, issued Jul. 12, 1994 to Bernoux, et al., and U.S. Pat. No. 5,166,752, issued Nov. 24, 1992 to Spanier, et al.

In the technique of spectroreflectometry an incident radiation beam reflects from a sample, and the intensity of the reflected radiation is analyzed to determine properties of the sample. The incident radiation includes multiple frequency components (or is monochromatic with a time-varying frequency), so that a spectrum of measured data (known as a reflectance spectrum or relative reflectance spectrum) including data regarding reflected intensity of incident radiation having each of at least two frequencies is measured. Systems for spectroreflectometry are described in U.S. Pat. No. 5,241,366 issued Aug. 31, 1993 to Bevis et al., and U.S. Pat. No. 4,645,349, issued Feb. 24, 1987 to Tabata, and the following U.S. patent applications assigned to the assignee of the present invention: U.S. Ser. No. 07/899,666, filed Jun. 16, 1992 (abstract published on Apr. 26, 1994 as the abstract of U.S. Pat. No. 5,306,916), and pending U.S. Ser. No. 08/218,975, filed Mar. 28, 1994.

Reflectance data (measured by spectroscopic ellipsometry, spectroreflectometry, or other reflection techniques) are useful for a variety of purposes. The thickness of various coatings (either single layer or multiple layer) on a wafer can be determined from spectroscopic ellipsometry data (indicative of the polarization of radiation reflected from the sample in response to incident radiation having known polarization state), or a reflectance spectrum or relative reflectance spectrum.

The reflectance of a sample (or sample layer) at a single wavelength can be extracted from a reflectance or relative reflectance spectrum. This is useful where the reflectance of photoresist coated wafers at the wavelength of a lithographic exposure tool must be found to determine proper exposure levels for the wafers, or to optimize the thickness of the resist to minimize reflectance of the entire coating stack.

The refractive index of a coating on a sample (or layer thereof) can also be determined by analysis of spectroscopic ellipsometry data (indicative of the polarization of radiation reflected from the sample, in response to incident radiation having known polarization state) or an accurately measured reflectance spectrum.

It would be useful for a variety of industrial applications to determine the thickness of a very small region of a very thin film (less than 30 angstroms in thickness) on a substrate from reflectance measurements (with sub-angstrom measurement repeatability) of the sample (e.g., where the sample is a semiconductor wafer and the very thin film is coated on a silicon substrate of the wafer). It would also be useful for a variety of industrial applications to obtain reflectance measurements using a single measurement system, and then analyze the measured data to determine the refractive index and thickness of a layer of a sample, where the layer has unknown thickness in a broad range from more than 10 microns to less than 10 angstroms.

It would also be useful to obtain reflectance measurements using a single measurement system, and then analyze the measured data to determine the refractive index and thickness of any selected layer of a multiple layer stack (where each layer has unknown thickness in a range from more than 10 microns to less than 10 angstroms). Such multiple layer stacks are often produced during the manufacture of semiconductor integrated circuits, with the stacks including various combinations of material such as $SiO_2$, $Si_3N_4$, TiN, Poly-Si, and a-Si.

Because of the tight tolerance requirements typically required in the semiconductor arts, an extremely accurate method and apparatus (e.g., having sub-angstrom repeatability) is needed for determining film thickness and refractive index measurements from reflectance data from a very small, and preferably compact region (e.g., a microscopically small region of size less than 40 micron×40 micron) of a wafer. However, it had not been known how to accomplish this using an ellipsometer with all-reflective optics (for use with broadband UV radiation). Conventional ellipsometers had employed transmissive optics to direct a beam at a sample, either with relatively high incidence angles (angles substantially greater than the zero degree incidence angle of "normally" incident radiation at a sample) as in above-cited U.S. Pat. No. 5,166,752, or with low incidence angle (normal or nearly normal incidence at the sample). The inventors have recognized that such transmissive optics are unsuitable for use with broadband radiation of ultraviolet (or UV to near infrared) wavelengths, and have also recognized that beams of such radiation incident on reflective ellipsometer components with high incidence angles undesirably undergo a large change in polarization upon reflection from each such reflective component. The inventors have also recognized that the change in beam polarization upon reflection from each optical component of an ellipsometer should be small relative to the polarization change (due to specific properties of the sample itself) occurring on reflection from the sample, and that such small polarization changes can be achieved by reflecting an ellipsometer beam from optical components of an ellipsometer only at small incidence angles (where the ellipsometer reflectively focuses the beam to a small, compact spot on the sample, with rays of the beam incident at the sample at a substantial range of high incidence angles).

Until the present invention, it had not been known how to meet the needs set forth in all three preceding paragraphs, and avoid the described limitations of the prior art set forth in these three preceding paragraphs.

SUMMARY OF THE INVENTION

The spectroscopic ellipsometry method and apparatus of the invention employs reflective optics to measure a small (and preferably compact) region of a sample (e.g., a microscopically small, square-shaped spot on the sample) by reflecting broadband radiation having a range of UV (and preferably also visible and near infrared) wavelengths from the region. The method and apparatus of the invention optionally also determines from the measurements the thickness and/or complex refractive index of a thin film on the sample (such as a layer of a multiple layer stack over a silicon substrate of a semiconductor wafer). Preferred embodiments of the inventive ellipsometer employ only reflective optics (along the optical path between the polarizer and analyzer) to avoid aberration and other undesirable effects that would otherwise result from transmission of broadband ultraviolet (UV) radiation through transmissive optics, and direct the beam so that it reflects with low incidence angle from each such reflective optical component. Preferred embodiments of the inventive ellipsometer focus a beam having elongated cross-section from an elliptical focusing mirror to a small, compact spot on the sample at a range of high incidence angles. The elliptical shape of the mirror surface reduces off-axis aberrations such as "coma" in the focused beam. Use of a reflective focusing element (rather than a transmissive lens) eliminates chromatic aberration in the focused beam.

Preferred embodiments of the invention include a spectrophotometer and an improved spectroscopic ellipsometer integrated together as a single instrument. In such integrated instrument, the spectrophotometer and ellipsometer share a broadband radiation source, and radiation from the source can be focused by either the spectrophotometer or the ellipsometer to the same focal point on a sample. Some of these embodiments include means for operating a selected one of the spectrophotometer and the ellipsometer. Others of the embodiments include means for supplying a portion of the radiation from the source to each of the spectrophotometer and ellipsometer subsystems, thus enabling simultaneous operation of both subsystems to measure the same small sample region.

Preferred embodiments of the inventive ellipsometer reflect a beam from a focusing mirror (where the beam has low incidence angle at the mirror) to focus a beam onto a small, square-shaped spot on a sample with high incidence angle. Preferably, the beam focused onto the spot has a substantial range of high incidence angles (e.g., the beam is a converging beam whose rays are incident at the sample with incidence angles in the range from about 63.5 degrees to 80.5 degrees), and a means is provided for selectively measuring only a portion of the radiation reflected from the sample after being incident at a single, selected high incidence angle (or narrow range of high incidence angles). In preferred implementations of these embodiments, a beam having elongated cross-section is focused from an elliptical focusing mirror to a compact spot on the sample, and the numerical aperture of the focusing mirror is sufficiently large to focus the reflected beam with a desired (sufficiently large) range of high incidence angles.

Preferred embodiments of the inventive ellipsometer also employ a rotating, minimal-length Rochon prism to polarize the broadband radiation beam incident on the sample (and also employ a fixedly mounted analyzer). The prism preferably has only the minimum length needed to enable the beam to pass through its clear aperture, because the prism's length is proportional to the amount of chromatic aberrations introduced by the prism. Alternatively, a phase modulator can be substituted for a rotating polarizer, or a fixedly mounted, minimal-length polarizing element can be employed with a rotating analyzer.

Other preferred embodiments of the inventive ellipsometer include a spectrometer which employs an intensified photodiode array to measure reflected radiation from the sample. Each photodiode in the array measures radiation, having wavelength in a different range, reflected from the sample. The intensified photodiode array may include an intensifier means, which preferably includes a top photocathode surface which emits electrons in response to incident photons, means for accelerating the electrons to a bottom phosphor surface, and a fiber optic coupler for directing photons emitted from the bottom phosphor to the photodiode array.

In some embodiments, the inventive ellipsometer includes a reference channel (in addition to a sample channel which detects radiation reflected from the sample). Illuminating radiation from the source is split into a sample beam and a reference beam, preferably by a bifurcated optical fiber. The sample beam reflects from the surface of a sample and is directed to the sample channel detector. The reference beam does not reflect from the sample, but is directed to the reference channel detector. By processing reference signals from the reference channel detector, as well as signals from the sample channel detector, the thickness of a very thin film on the sample (or the sample's refractive index) can be more accurately determined.

The invention has many applications, such as measuring refractive indices, measuring film thicknesses, and determining lithographic exposure times, and (in embodiments including a spectrophotometer) measuring reflectance spectra.

DESCRIPTION OF THE PREFERRED EMBODIMENTS

Figure 1:
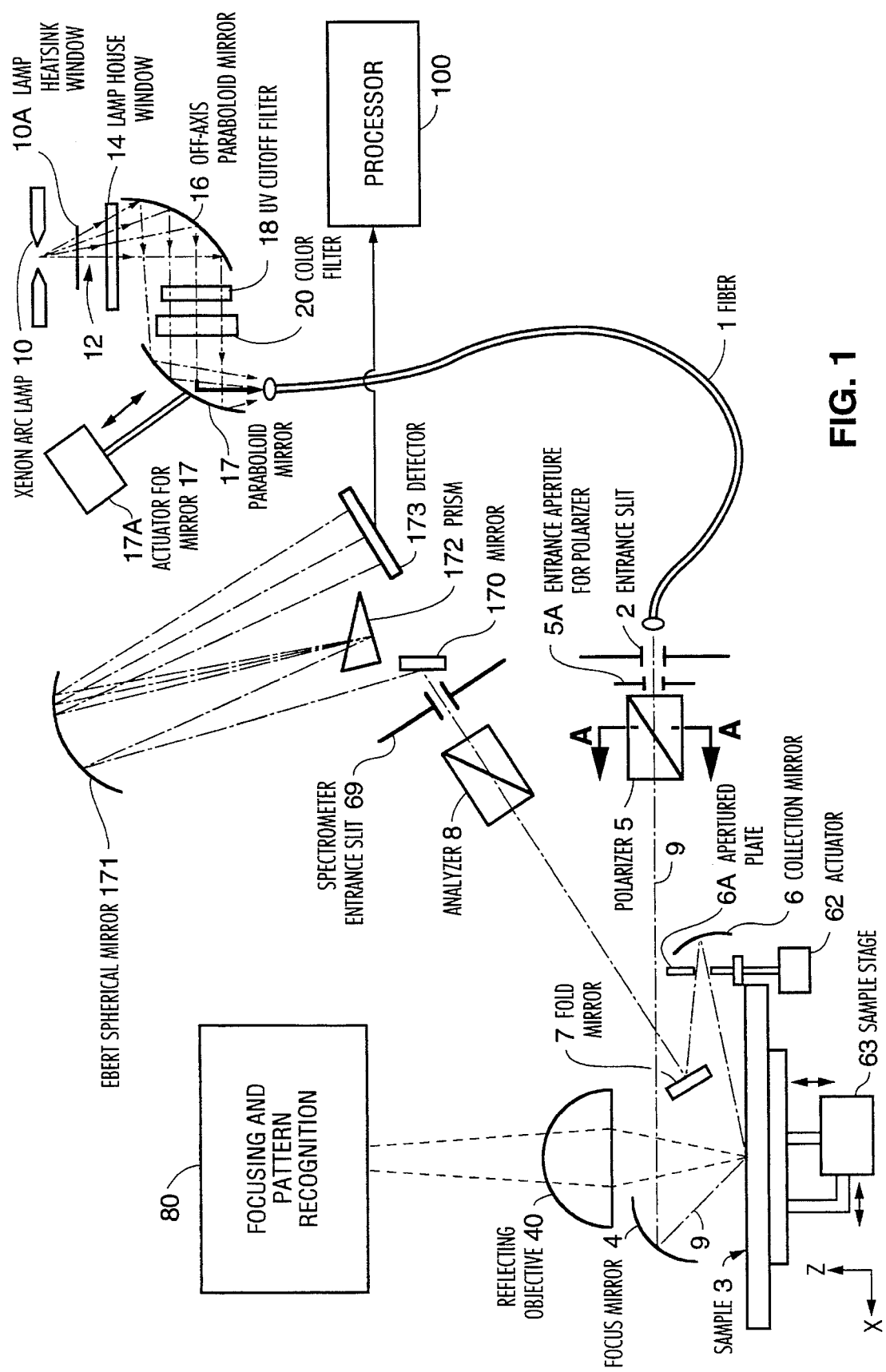
FIG. 1 is a schematic diagram of a preferred embodiment of the spectroscopic ellipsometer of the invention.

Throughout the specification, including in the claims, the phrase "incidence angle" of radiation at a surface denotes the angle between the normal to the surface and the propagation direction of the radiation. Thus, radiation with normal incidence at a sample surface has an incidence angle of zero degrees, and radiation with grazing incidence at such surface has an incidence angle substantially equal to 90°. Throughout the specification, including in the claims, the phrase "high incidence angle" denotes an incidence angle greater than 30°. Throughout the specification, including in the claims, the phrase "broadband radiation" denotes radiation whose frequency-amplitude spectrum includes two or more different frequency components. For example, broadband radiation may comprise a plurality of frequency components in the range from 230 nm to 850 nm, or a plurality of frequency components in the range from 400 nm to 700 nm.

A preferred embodiment of the focused beam spectroscopic ellipsometer of the invention will be described with reference to FIG. 1. The focused beam spectroscopic ellipsometer of FIG. 1 includes several subsystems:

optical and signal processing components (components 1, 4–6, 6A, 7, 8, 10, 10A, 14, 16, 17, spectrometer components 69, 170, 171, 172, and 173, and processor 100) for measuring polarized radiation of beam 9 which has reflected from a small spot on sample 3, and for processing the measured data;

focusing and pattern recognition components (including objective 40 and subsystem 80) for controlling the focusing of beam 9 onto a desired small spot on sample 3, and optionally also for imaging sample 3 (or a selected portion of sample 3) and recognizing a pattern in such image; and sample stage 63 (for moving sample 3 relative to the ellipsometer's optical components and relative to objective 40).

Beam 9 (radiation emitted from lamp 10 and then polarized in polarizer 5) is reflected from sample 3 through a slit in aperture plate 6A to collection mirror 6, is then reflected from mirror 6 to mirror 7, and is then directed by mirror 7 through analyzer 8 into a spectrometer. The spectrometer (to be described in detail below) comprises entrance slit member 69, folding mirror 170, Ebert spherical mirror 171, prism 172, and detector 173. Alternatively, an Ebert-Fastie or Czerny-Turner spectrometer can be employed.

Radiation (e.g., from lamp 10) is reflected from sample 3 back to objective 40, and is focused by objective 40 onto optical elements or sensors within subsystem 80 (for use in performing pattern recognition, controlling the focusing of beam 9 onto sample 3, and optionally displaying an image of all or part of the sample). The FIG. 2 apparatus can be employed to implement the functions of subsystem 80 and objective 40.

Sample 3 is typically a semiconductor wafer with at least one thin layer 3a (shown in FIG. 2) on a substrate. Other samples (or sample substrates), such as glass plates used in flat panel displays, may also be used.

The illumination subsystem of FIG. 1 includes lamp 10 (preferably a xenon arc lamp including heatsink window 10A) which emits radiation beam 12 having a broad range of frequency components in the UV, visible, and near infrared wavelength bands, a lamp housing including lamp housing window 14, off-axis paraboloid mirror 16, UV cutoff filter 18 and color filter 20 (both discussed below with reference to FIG. 2), paraboloid mirror 17, and optical fiber 1. Fiber 1 has an inlet end for receiving beam 12, after beam 12 has reflected from mirror 16, passed through UV cutoff filter 18 and color filter 20, and then reflected from mirror 17. Beam 12 propagates through fiber 1 to entrance slit member 2 and then through the entrance slit in member 2. Mirrors 16 and 17 preferably have identical design.

Lamp 10 emits beam 12 through heatsink window 10A and then through lamp housing window 14, to mirror 16. Windows 10A and 14 are unnecessary for optical reasons, but function to keep lamp cooling air from being drawn through the optical path, thereby avoiding noise due to shimmering of the arc image. A xenon arc lamp is preferred over other lamps such as tungsten or deuterium lamps, because a xenon lamp will produce radiation having a flatter spectrum in the wavelength range from UV to near infrared. Alternatively, a tungsten lamp and a deuterium lamp can be used in combination to cover the substantially the same spectrum covered by a xenon lamp, but this lamp combination typically has a gap in brightness in the mid-UV wavelengths. Brightness of the spectrum is important, because with less intensity, reflected radiation must be collected for longer periods. The lower intensities slow the measurement process. In alternative embodiments, a lamp is chosen which emits broadband UV radiation without emitting significant visible or near infrared radiation.

Preferably, optical fiber 1 is made of fused silica, a UV transmitting material, and has a core diameter of 365 microns.

Figure 2:
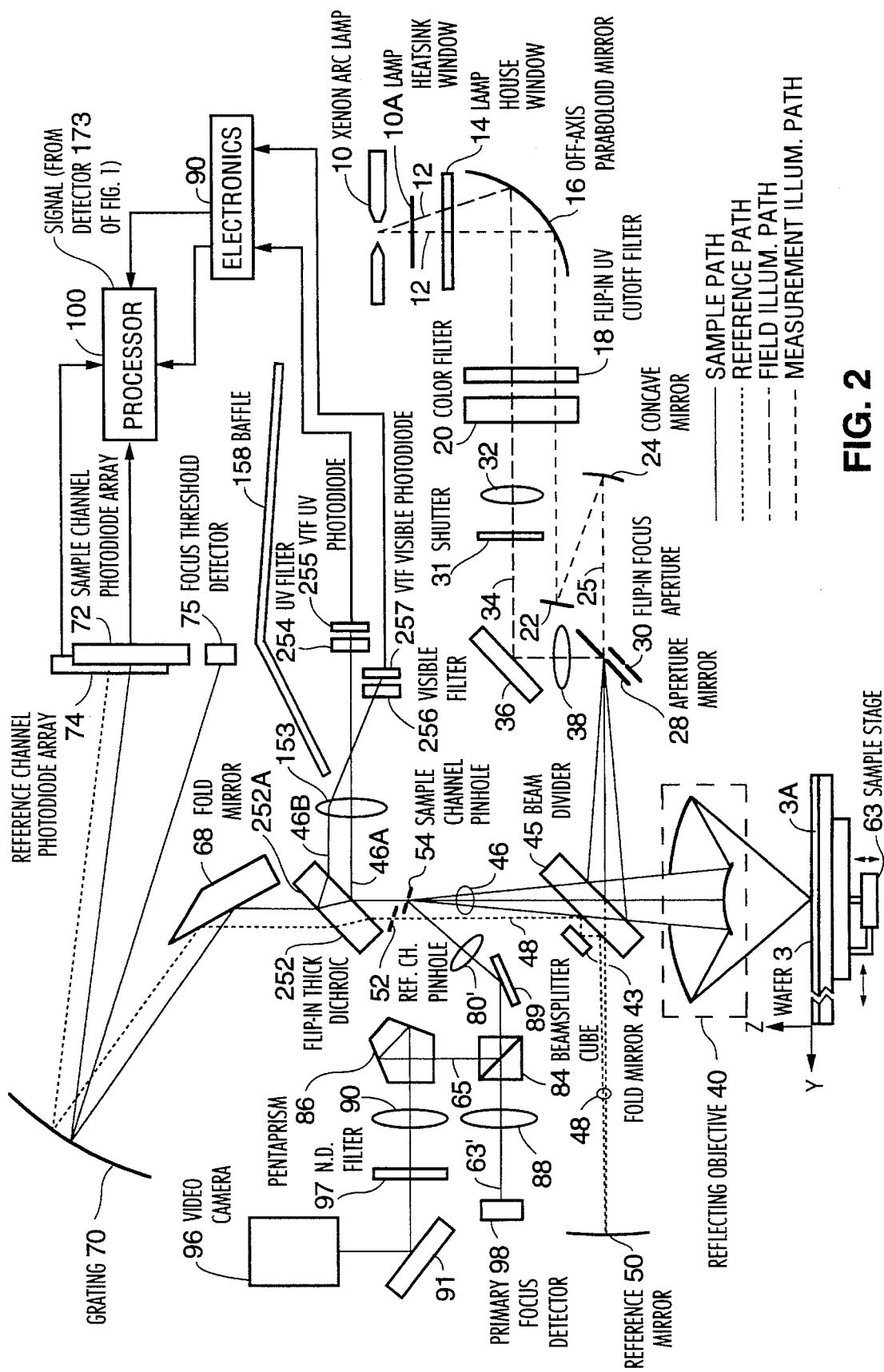
FIG. 2 is a schematic diagram of a spectrophotometer (different from the spectrophotometer shown in FIG. 14 which is preferred for integration with the inventive ellipsometer) which shares arc lamp 10, paraboloid mirror 16, filters 18 and 20, sample stage 63, and processor 100 with the FIG. 1 apparatus. By controlling the position of mirror 17 (shown in FIG. 1), radiation from lamp 10 can be directed to sample 3 by either elements 17, 1, 2, 5, and 4 of the ellipsometer of FIG. 1, or by elements 18, 32, 36, 28, 30, 45, and 40 of the spectrophotometer of FIG. 2.
Figure 14:
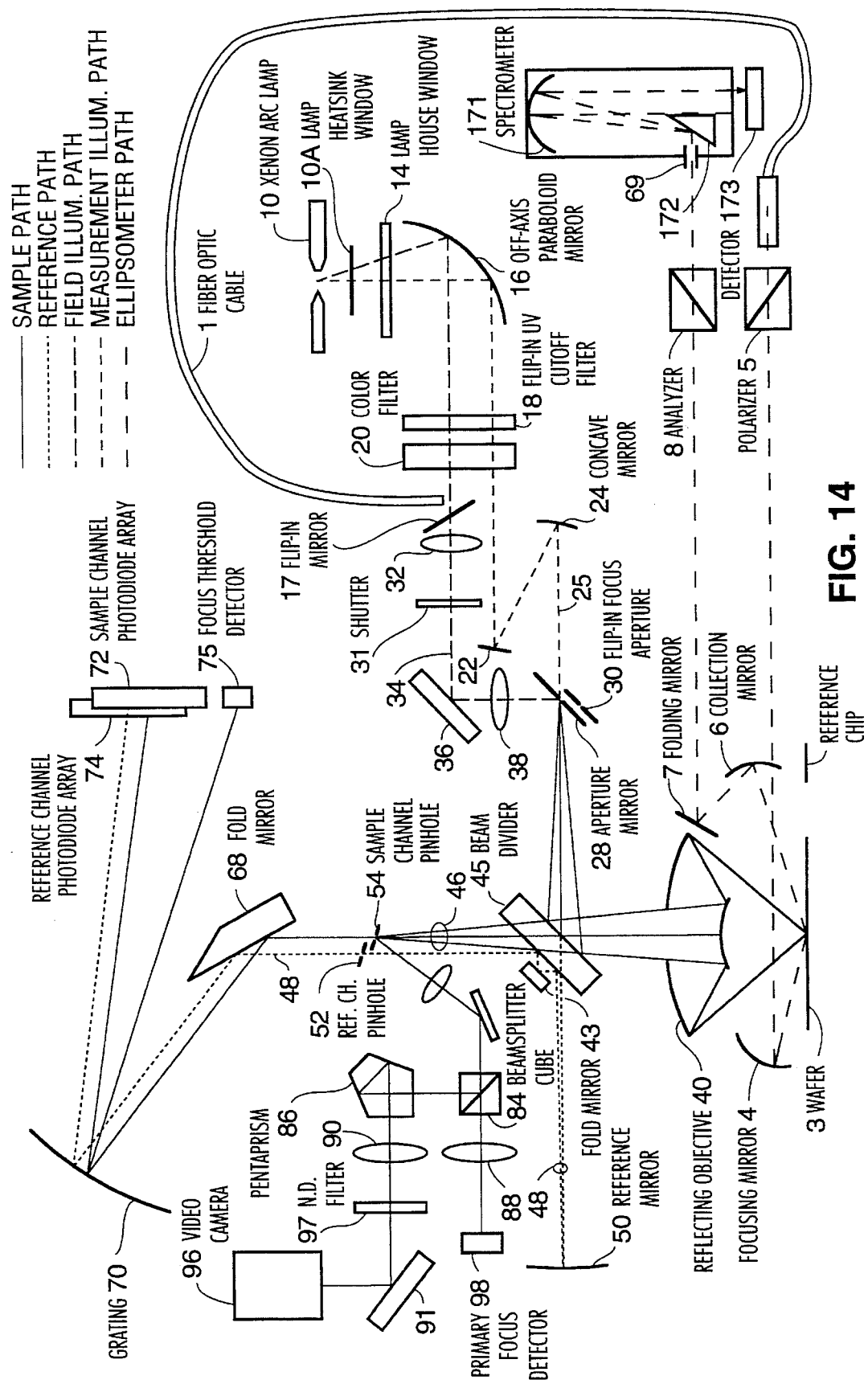
FIG. 14 is a schematic diagram of a preferred embodiment of the invention which is a spectrophotometer integrated together with a spectroscopic ellipsometer. The spectrophotometer shares arc lamp 10, paraboloid mirror 16, filters 18 and 20, sample stage 63, and processor 100 with the ellipsometer. By controlling the position of mirror 17, radiation from lamp 10 can be directed to sample 3 from either elements 1, 5, and 4 of the ellipsometer, or from elements 32, 36, 38, 28, 30, 45, and 40 of the spectrophotometer.

The illumination subsystem optionally includes actuator 17A connected to mirror 17. Actuator 17A operates to move mirror 17 between a first position (shown in FIG. 1) in which it reflects beam 12 from mirror 16 toward the inlet end of fiber 1, and a second position (not shown in FIG. 1). In such second position, mirror 17 is outside the optical path of beam 12 and thus does not impede propagation of beam 12 from mirror 16 to a spectrophotometer (e.g., to lens 32 and mirror 22 of the spectrophotometer of FIG. 2). Such spectrometer is not shown in FIG. 1, but is shown in FIG. 2, and is preferably integrated with the inventive ellipsometer (as shown in FIG. 14). The spectrophotometer of FIG. 2, and the manner in which it is integrated with the FIG. 1 ellipsometer, will be described below in detail.

Figure 3:
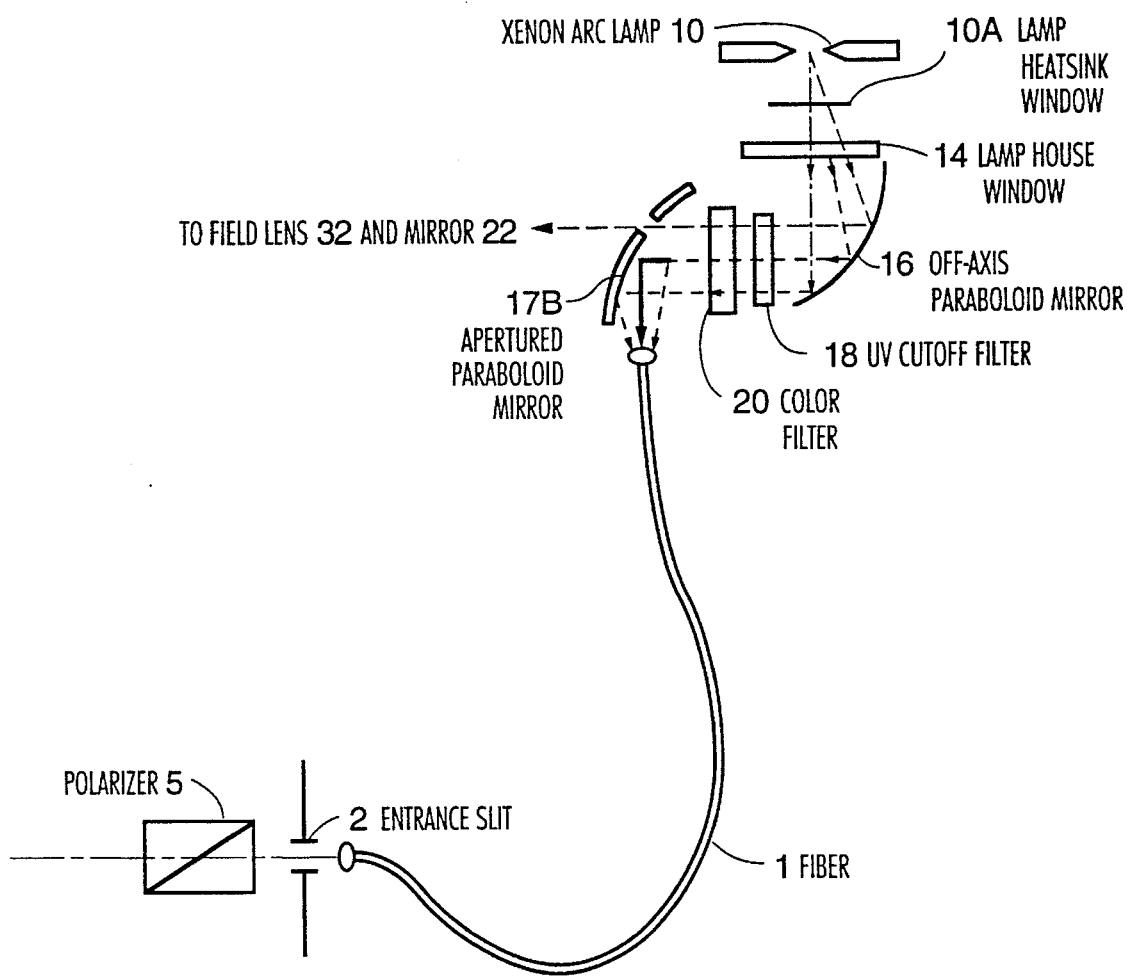
FIG. 3 is a schematic diagram of a portion of an alternative embodiment of the invention which includes both a spectroscopic ellipsometer (a variation on the system shown in FIG. 1), and the spectrophotometer of FIG. 2, in which the spectroscopic ellipsometer and spectrophotometer are simultaneously operable.

Also described below (with reference to FIG. 3) is a variation on the FIG. 1 apparatus in which an apertured paraboloid mirror 17B (of FIG. 3) is substituted for mirror 17, to split the radiation from lamp 10 into two portions to enable simultaneous operation of both an ellipsometer and a spectrophotometer.

With reference again to FIG. 1, the sample illuminating radiation enters polarizer 5 after propagating from fiber 1 through the entrance slit in member 2. The portion of this radiation which propagates through polarizer 5 emerges from polarizer 5 as polarized beam 9. Polarized beam 9 is a measurement beam having a known polarization state. Polarizer 5 preferably has apertured plate 5A, with a circular aperture therethrough, positioned at its input face to limit the size of the polarized beams so that the two polarizations do not overlap. The diameter of this circular aperture is about 1 mm in one preferred embodiment in which the distance between entrance slit member 2 and polarizer 5 is about three inches.

Entrance slit member 2 is a substrate (preferably made of stainless steel) through which an elongated, rectangular entrance slit (60 microns×500 microns) has been etched. Because of the elongated shape of the entrance slit, elliptical focusing mirror 4 images the entrance slit as a small (25 micron×25 micron), compact (square-shaped) spot on sample 3, by reflectively focusing the beam 9 onto sample 3 at high incidence angle. Polarized beam 9 is incident at mirror 4 with a low incidence angle. Due to its orientation and the shape of its elliptical focusing surface, mirror 4 images the entrance slit Mirror 4 has a numerical aperture (0.15 or greater, in preferred implementations of FIG. 1) selected so that the rays of beam 9 reflected from mirror 4 will be incident at sample 3 with a desired range (preferably, a substantial range) of high incidence angles. In preferred implementations of FIG. 1 in which the numerical aperture of mirror 4 is 0.15, the range of high incidence angles (at which beam 9 strikes sample 3) is the range from about 63.5 degrees to about 80.5 degrees (from the normal to the surface of sample 3). This range desirably includes incidence angles near Brewster's angle for crystalline silicon (about 75° at 630 nm wavelength) so that the instrument displays a high degree of sensitivity for film variations on silicon substrates.

The preferred shape of focusing mirror 4's reflective surface is elliptical. As is well known, an elliptical mirror has two foci. In embodiments in which mirror 4 is an elliptical mirror, sample 3 should be positioned at one focus of the mirror and the entrance slit (through member 2) should be positioned at the other focus of the mirror.

The elongated shape of the entrance slit in member 2, with the described design and orientation of mirror 4, results in focusing of beam 9 onto a small, compact (preferably square-shaped) spot on sample 3 with high incidence angle.

In alternative embodiments of the invention, other combinations of an entrance slit and a focusing mirror are employed (in place of elements 2 and 4 of FIG. 1) to focus a beam onto a small (but not compact) spot on sample 3 with a substantial range of high incidence angles.

Designing the reflective surface of mirror 4 to have its preferred elliptical shape (rather than a spherical shape, for example) reduces off-axis aberrations (such as the aberration known as "coma") in the focused beam incident on the sample. Use of a reflective elements (mirrors 4, 6, and 7) between the polarizer and analyzer, rather than transmissive lenses, minimizes chromatic aberration in the analyzed beam which reaches spectrometer entrance slit member 69.

Collection mirror 6 receives that portion of the diverging beam reflected from sample 3 which passes through an aperture in apertured plate 6A. Mirror 6 preferably has a focal length of 70 mm and a diameter of 20 mm. Mirror 6, because it is spherical, introduces coma into the beam. However, the aberration spreads the beam in a direction parallel to the long axis of the spectrometer entrance slit so it does not affect the light transmission properties of the instrument. In addition the spectrometer entrance slit is preferably rotated by approximately 5 degrees in a plane perpendicular to the surface normal in order to better pass the aberrated beam.

The aperture in plate 6A is preferably elongated, and oriented to pass only the radiation which has reflected from sample 3 after reaching the sample at a single incidence angle (or narrow range of incidence angles). The aperture is preferably about 2 mm tall (in the Z-direction shown in FIG. 1) and 20 mm wide, and oriented so as to pass the radiation reflected from sample 3 at an angle in the range from 75° to 77°, while plate 6A blocks all other radiation reflected from sample 3. Thus, where beam 9 strikes sample 3 with a substantial range of high incidence angles, apertured plate 6A passes (for propagation to analyzer 8 and then measurement by detector 173) only the radiation reflected from sample 3 after striking the sample at a narrow subset of the substantial range of high incidence angles.

In accordance with the invention, actuator 62 can position plate 6A at any selected one of a range of positions in the optical path of reflected beam 9, so that the slit (aperture) through plate 6A will pass only those rays of the reflected beam which have reflected from sample 3 at incidence angles in a selected narrow range. For example, actuator 62 can be operated to move plate 6A (downward along the Z-axis in FIGS. 1 and 8) from the position shown in FIG. 1 (and FIG. 8) to a position in which the slit through plate 6A passes radiation reflected from sample 3 at an angle in the range from 77° to 79° (and in which plate 6A blocks all other radiation reflected from the sample). Plate 6A and actuator 62 are shown in both FIGS. 1 and 8, but the manner in which plate 6A blocks some of the radiation reflected from sample 3 is shown more clearly in FIG. 8.

To measure a complicated film stack, it is necessary to perform multiple independent measurements at different settings of one or more measurement parameters (such as wavelength or incidence angle). Spectroscopic ellipsometric measurement (at a fixed incidence angle) simultaneously provides data for multiple wavelengths of radiation reflected from the sample. Varying incidence angle in a sequence of spectroscopic ellipsometric measurements provides data about the sample which usefully supplements the data obtained at one fixed incidence angle.

The width of the slit through apertured plate 6A determines the spreading of the incidence angles associated with the measured portion of the radiation reflected from sample 3, and the location of the slit's center determines the average incidence angle associated with the measured portion of such reflected radiation. Preferably, actuator 62 includes means for controlling both the slit width and the location of the slit's center. However, in some embodiments of the invention, the slit width and/or the location of the slit center are fixed. In embodiments in which the location of the slit center can be controlled, such location will typically be chosen to be close to Brewster's angle for the sample being measured. For example, when the sample is a flat panel display comprising films deposited on a glass substrate, it is useful to locate the slit center so that plate 6A passes only rays reflected from the flat panel display after being incident at angles in a narrow range centered at 57° (since Brewster's angle for glass is about 57° at visible wavelengths). The latter embodiment would require substitution of a differently shaped focusing mirror for above-described elliptical focusing mirror 4 (since above-described mirror 4 could not focus radiation to sample 3 at incidence angles close to 57 degrees).

Figure 6:
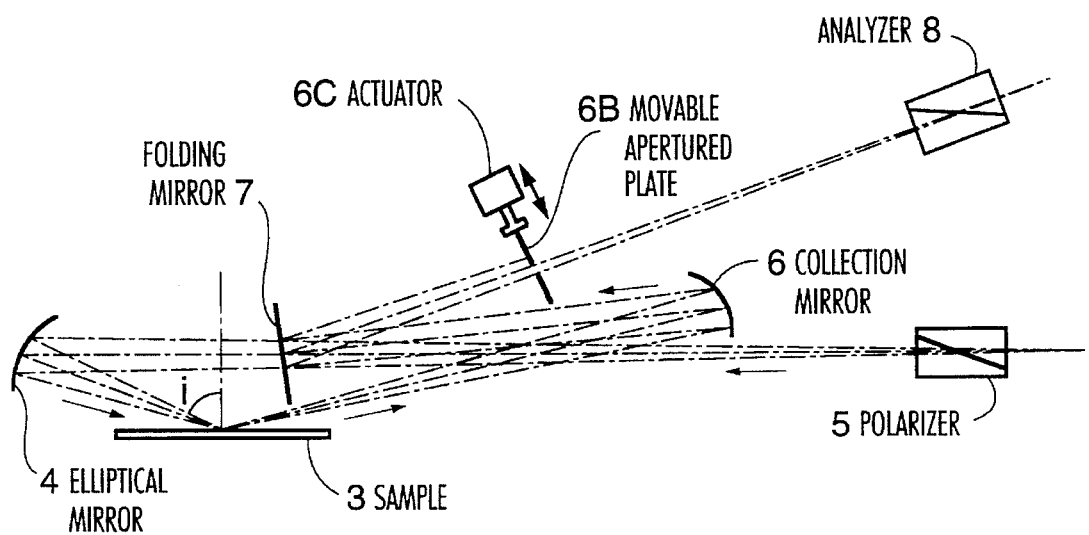
FIG. 6 is a schematic diagram of a portion of another alternative embodiment of the inventive ellipsometer (a variation on the system shown in FIG. 1).

Apertured plate 6A functions as an incidence angle selection element. An alternative position for the incidence angle selection element of the invention is shown in FIG. 6, and another such alternative position is between mirror 6 and mirror 7. In FIG. 6, the incidence angle selection element is movable apertured plate 6B, which is located between folding mirror 7 and analyzer 8 (in contrast with plate 6A of FIG. 1, which is located between sample 3 and mirror 6). Actuator 6C of FIG. 6 controls the location of the center of the slit through plate 6B, so that when radiation reflected from sample 3 at a substantial range of angles reaches plate 6B, only a portion of such radiation (i.e., the radiation reflected from sample 3 at a selected, narrow subrange of the "substantial range") will pass through plate 6B's slit. The dimensions of apertured plate 6B and the slit therethrough can (but need not) be identical to those of apertured plate 6A. Actuator 6C can (but need not) be identical to actuator 62 of FIG. 1.

Figure 7:
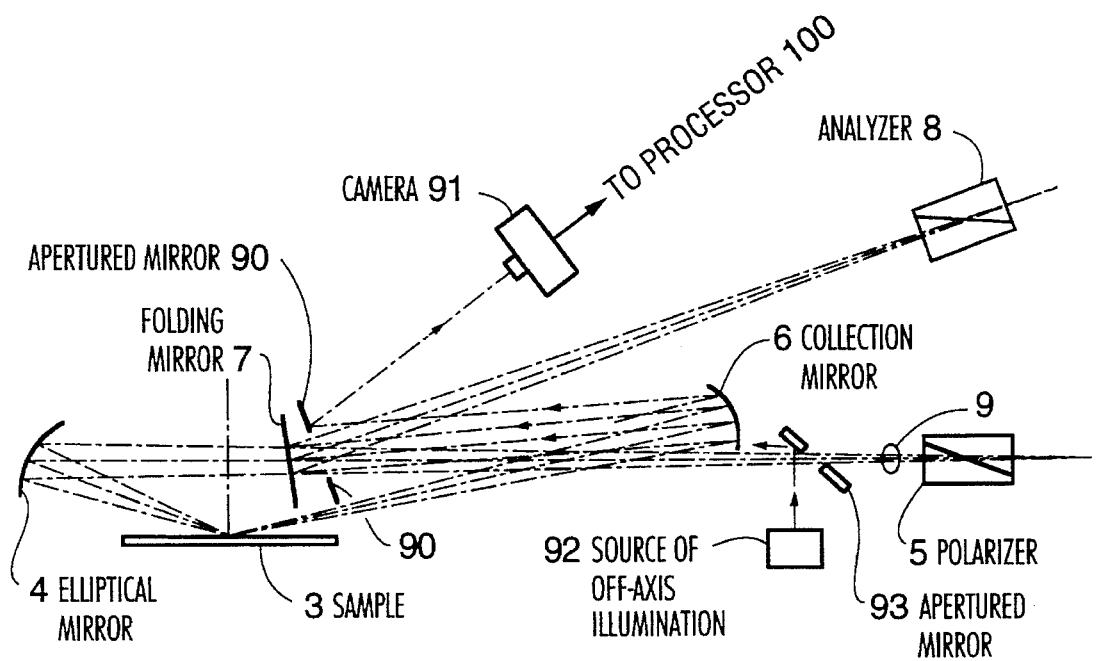
FIG. 7 is a schematic diagram of a portion of another alternative embodiment of the inventive ellipsometer (a variation on the system shown in FIG. 1).
Figure 8:
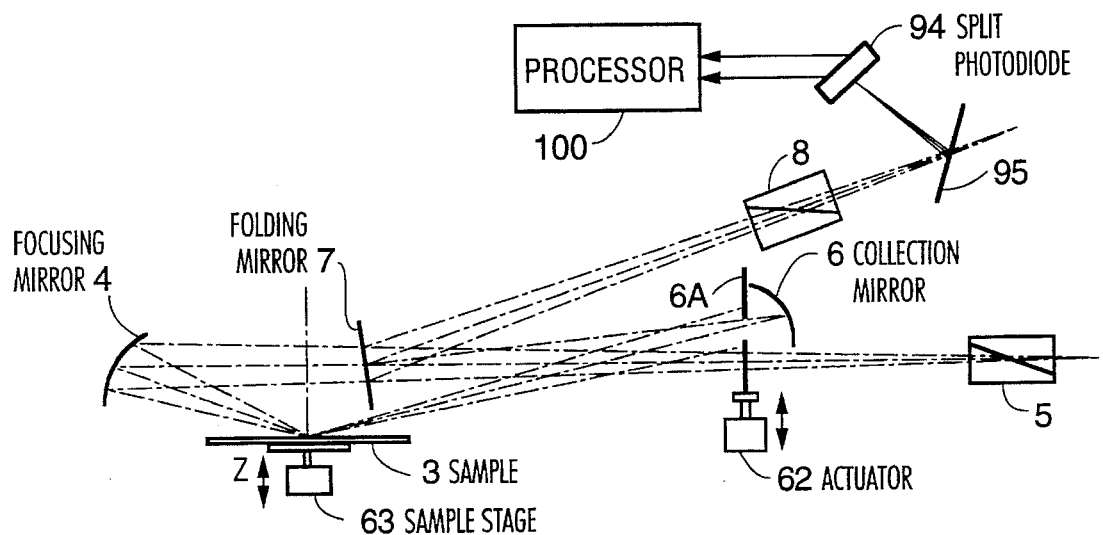
FIG. 8 is a schematic diagram of a portion of another alternative embodiment of the inventive ellipsometer (a variation on the system shown in FIG. 1).

It should be understood that in each of FIGS. 6, 7, and 8, the polarized beam emitted from polarizer 5 propagates directly to mirror 4 without interacting with mirror 7. Mirror 7 is positioned so as to reflect (toward analyzer 8) only radiation that has already reflected from mirror 60

Figure 15:
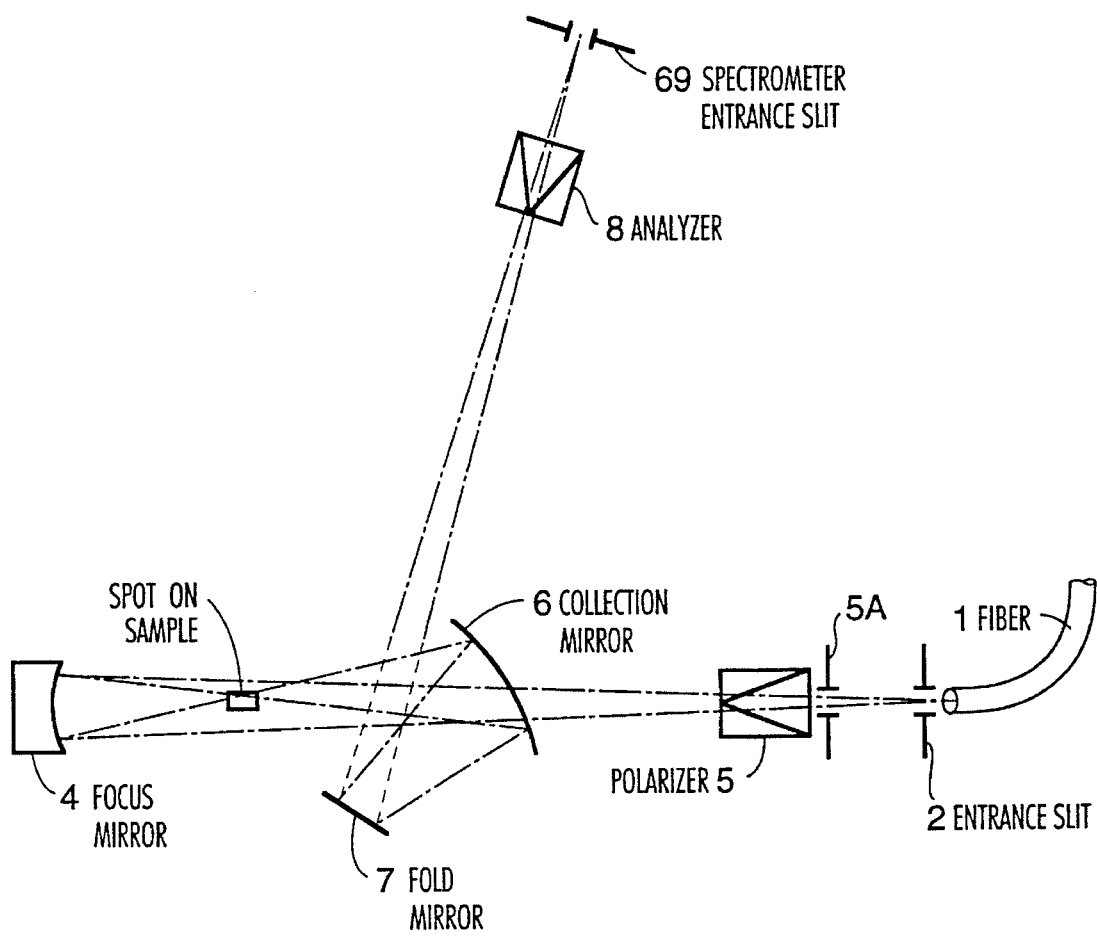
FIG. 15 is a simplified top view of a portion of the spectroscopic ellipsometer of FIG. 1.

With reference again to FIG. 1 (and to FIG. 15 which is a simplified top view of a portion of the FIG. 1 system), either polarizer 5 or analyzer 8 is rotated (about the optical axis) during measurement operations. In embodiments in which polarizer 5 is rotated and analyzer 8 remains fixed, each of polarizer 5 and analyzer 8 is preferably a minimal-length Rochon prism of the type shown in FIGS. 4 and 5. The Rochon prism consists of two pieces separated by interface 5C, and splits the incident beam into two components: an ordinary polarized through beam, and an extraordinary polarized beam that is deflected by an angle of 1.6 degrees (a deflection of at least 1.5 degrees is preferred for implementing the invention). The ordinary polarized beam is employed as beam 9 (which is focused by mirror 4 on the sample). Since it is desired to focus beam 9 on a small spot on the sample (e.g., to measure film thickness at such spot), no motion in the ordinary polarized "through" beam emitted from prism 5 can be tolerated. Typically, the rotation of prism 5 must be controlled so that the through beam deviation is constrained to be less than 30 seconds of arc, in order to restrict the motion of the spot on the sample to less than 1 micron. In some embodiments, through beam deviation of up to one minute of arc can be tolerated.

Figure 4:
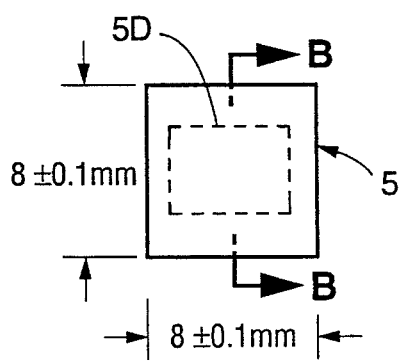
FIG. 4 is a simplified cross-sectional view (taken along line A—A of FIG. 1) of a preferred embodiment of polarizer 5 of FIG. 1.
Figure 5:
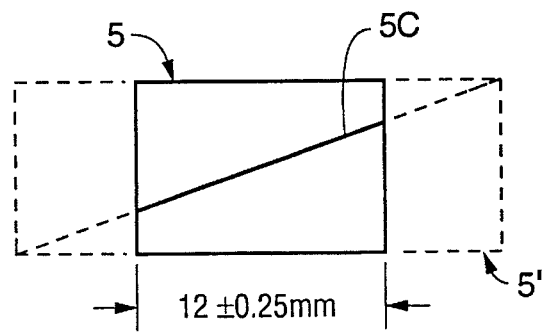
FIG. 5 is a simplified cross-sectional view (taken along line B—B of FIG. 4) of the FIG. 4 embodiment of polarizer 5 (showing, for purposes of comparison, a conventional polarizer 5' in phantom view).

With reference to FIGS. 4 and 5, the preferred Rochon prism embodiment of polarizer 5 (and analyzer 8) has only the minimum length (along the axis of "through beam" propagation) needed to enable the beam to pass through its clear aperture, because the prism's length is proportional to the amount of chromatic aberrations introduced by the prism.

The area within polarizer 5 bounded by rectangular perimeter 5D in FIG. 4 is the projection of interface 5C onto the plane of FIG. 4, and is what is referred to as the "clear aperture" of polarizer 5. As shown in FIG. 1, plate 5A having an entrance aperture therethrough should be positioned along the optical path between entrance slit element 2 and polarizer 5, so that the aperture through plate 5A determines the diameter of the beam (which has passed through the entrance slit through element 2) which passes through polarizer 5. The length of polarizer 5 should be the minimum length (assuming a fixed angle between interface 5C and the right face of polarizer 5 in FIG. 5) which causes the clear aperture to be as large as the cross-section of the beam incident on polarizer 5 (so that the entire beam passing through plate 5A to polarizer 5 can propagate through the clear aperture). It will be apparent to those of ordinary skill that the mechanical constraints inherently faced in designing and mounting a polarizer will also affect the minimum practical length for polarizer 5, and that varying the position of prism 5 (in the FIG. 1 system) will affect the preferred size of the aperture through plate 5A.

Rochon prism 5 of FIG. 5 (which is preferred for use as polarizer 5 and analyzer 8 in FIG. 1) has a length (along the axis of through beam propagation) equal to 12 mm, with a tolerance of plus or minus 0.25 mm. In contrast, the length of a conventional, commercially available Rochon prism 5' (shown in phantom view in FIG. 5) is approximately 25 mm. As shown in FIG. 4, the Rochon prism 5 preferred for use as polarizer 5 in FIG. 1, has a square cross-section (in a plane perpendicular to the axis of through beam propagation) with sides of length 8 mm, with a tolerance of plus or minus 0.1 mm. The preferred Rochon prism of FIGS. 4 and 5 preferably uses UV transmitting crystalline quartz, is optically contacted for enhanced UV transmission, introduces wavefront distortion of less than one quarter of a wavelength (at 633 nm), has transmittance in the UV of at least 40% (for two open polarizers at 230 nm) when used with an unpolarized light source, and has uncoated faces.

To measure a sample, analyzer 8 typically remains fixed while polarizer 5 rotates about the optical axis. Analyzer 8 is mounted so as to be free to rotate into a different angular orientation when a new sample is placed in the instrument (or when a new measurement is to be conducted on the same sample). This technique of "analyzer tracking" is well known in the field of ellipsometry.

Alternative embodiments of the invention employ an alternative type of polarizer (and analyzer), such as a Glan-Taylor polarizer (which is a polarizer well known in the art). Other embodiments employ a phase modulator (such as a photoelastic modulator) in place of a rotating polarizer. Other alternative embodiments employ an analyzer that rotates during measurement of a sample, with a fixedly mounted, minimal-length polarizer (or another fixedly mounted polarizer).

With reference again to FIG. 1, we next discuss the spectrometer of the inventive spectroscopic ellipsometer, which comprises entrance slit member 69, folding mirror 170, Ebert spherical mirror 171, prism 172, and detector 173. Slit member 69 is made of the same material as above-described entrance slit member 2. The spectrometer entrance slit through member 69 is preferably an elongated slit of size 230 microns by 1200 microns (the beam is focused to a spot on sample 3 which is smaller than this entrance slit, and so the beam passes through the entrance slit unobstructed). The spectrometer is of a standard Ebert design, in which the broadband beam passed through member 69 (from analyzer 8) reflects from mirror 170 to mirror 171, and from mirror 171 to prism 172. The beam components having different wavelengths are refracted in different directions from prism 172 to mirror 171, and from mirror 171 to detector 173. Mirror 171 images the entrance slit (through member 69) to detector 173, and mirror 171 preferably has a focal length of 250 mm. In preferred embodiments, detector 173 is essentially a linear array of photodiodes, with each photodiode measuring radiation in a different wavelength range. Preferably the radiation includes components with wavelength in the range from 230 nm to 850 nm, detector 173 includes 512 photodiodes, and each photodiode (or set of adjacent photodiodes) receives radiation in a different segment of the 230–850 nm wavelength range. For example, the resolution of the photodiode array may be limited to groups of three to five adjacent photodiodes, in the sense that each resolvable radiation element has a width of three to five photodiodes.

Figure 13:
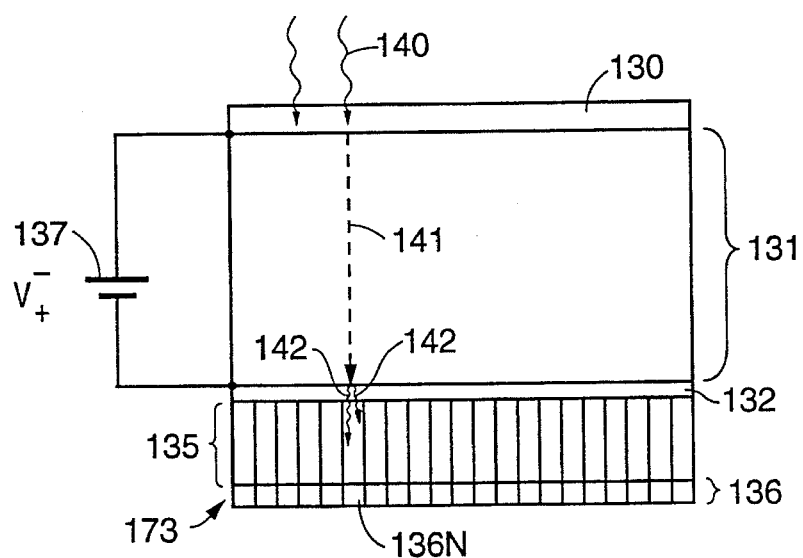
FIG. 13 is a simplified cross-sectional view of a preferred embodiment of detector 173 (shown in FIGS. 1 and 12).

Preferably, detector 173 is an intensified photodiode array of the type shown schematically in FIG. 13. Important benefits of the FIG. 13 design include the ability to measure low-intensity reflected radiation deep into the UV range, and improved sensitivity at all wavelengths of the reflected broadband radiation. The intensified photodiode array of FIG. 13 includes a linear photodiode array 136, and an intensifier assembly including top photocathode layer 130 which emits electrons in response to incident photons, bottom phosphor layer 132 (oriented parallel to layer 130), means 131 for holding layer 130 at fixed spacing relative to layer 132, voltage source 137 for maintaining a potential difference V between layers 130 and 132 (such that electrons emitted from layer 130 are accelerated toward layer 132 in the electrical field due to voltage V), and fiber optic coupler plate 135 between layer 132 and photodiode array 136 (for directing photons, emitted from phosphor layer 132 in response to accelerated electrons from layer 130, to photodiode array 136). Linear array 136 preferably includes 512 photodiodes. In operation, photons 140 (of a particular wavelength) reflected from mirror 171 are incident at photocathode layer 130. In response, electrons 141 are ejected from layer 130, and these electrons are accelerated vertically downward (in FIG. 13) to phosphor layer 132. In response to these electrons, layer 132 emits photons 142 of a particular wavelength (not necessary the same as that of photons 140). One of the optical fibers of fiber optic coupler plate 135 (all fibers of which are vertically oriented in FIG. 13) directs photons 142 to a particular photodiode (photodiode 136N) of photodiode array 136. Each photodiode in array 136 measures radiation of a different wavelength (or radiation in a different, and typically narrow, range of wavelengths). In a preferred embodiment, a commercially available intensified photodiode array assembly is employed as the FIG. 13 detector (e.g., a photodiode array available from the Japanese company Hammamatsu, to which an intensifier, known as Part Number BV2532QZ-15 available from Proxitronics, is mated). The photodiode array of this commercially available product has 512 photodiodes, which independently measure 512 different wavelengths. Alternative embodiments of the detector of the inventive ellipsometer detect radiation in more than 512 or less than 512 different wavelength channels. Another alternative embodiment of detector 173 is a UV enhanced CCD array detector.

We next describe two embodiments of an autofocus assembly for the inventive ellipsometer. One such assembly is shown in FIG. 7, and the other will be described with reference to FIGS. 8–11.

Figure 9:
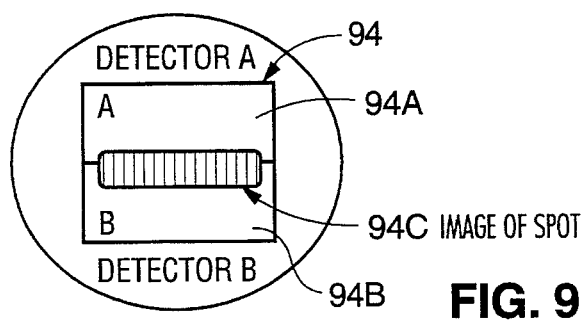
FIG. 9 is a front elevational view of detector 94 of FIG. 8.

The autofocus assembly of FIGS. 8–11 includes split photodiode detector 94, which receives a substantially focused image of the spot to which beam 9 is focused on sample 3. This image is provided by positioning beamsplitting mirror 95 along the optical path between analyzer 8 and spectrometer entrance slit element 69 (of FIG. 1) to divert a portion of the beam transmitted through analyzer 8 to detector 94. Detector 94 has two photodiodes, 94A and 94B, which are best shown in FIG. 9. Each of photodiodes 94A and 94B provides a measured intensity signal to processor 100. Processor 100 processes these signals in the manner described below. Detector 94 is positioned so that an entire substantially focused image (94C) of the spot can be projected onto photodiodes 94A and 94B, with approximately half of image 94C projected onto each of photodiodes 94A and 94B as shown in FIG. 9.

The reason for use of split photodiode detector 94 can be appreciated by considering the following explanation, which contrasts a conventional autofocus system with the autofocus assembly of FIG. 8.

Figure 10:
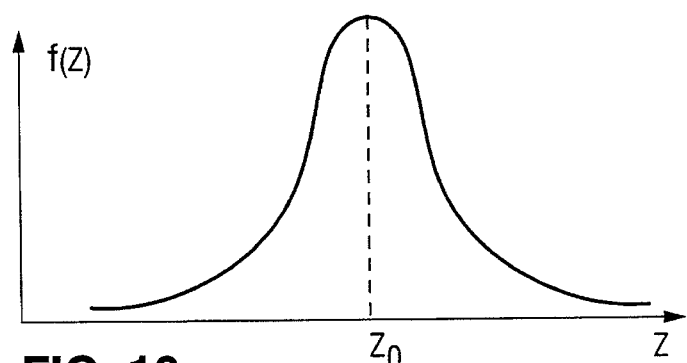
FIG. 10 is a graph of a conventionally defined focus signal, f(z), which is a function of position of sample 3 along the z-axis of FIG. 8, and which could be generated using conventional means in a variation on the FIG. 1 system in which both polarizer 5 and analyzer 8 remain fixed (and do not rotate).

In a conventional autofocus system, the sample stage scans in one direction (typically the z-direction as shown in FIGS. 1 and 2) to find the best focus position, while a single detector monitors radiation reflected from the sample. The detector's output signal, f(z), is called a focus signal, and is a function of sample position. There are usually one or two extrema in the focus signal, depending on the optical system configuration. The best focus position is usually determined by the position of an extremum in the focus signal (as shown in FIG. 10).

However, this conventional autofocus technique is not useful with the spectroscopic ellipsometer of FIG. 1 (or the mentioned variations thereon) because the sample illuminating radiation from the rotating polarizer (or photoelastic modulator) has a periodically modulated intensity. Thus, the signal recorded by the single detector is a time-varying function even when the sample stage is kept stationary. For a rotating polarizer (with a fixed sample position), the recorded signal is $I(t) = I_o [1 + A\cos(2wt) + B\sin(2wt)]$, where w is the angular frequency of the rotating polarizer, $I_o$ is a constant, and A and B are sample-dependent constants. The resulting focus signal F(z,t), measured by a single detector with both rotation of the polarizer and variation of sample position, is the product of the conventional focus signal f(z) and the signal I(t):

$F(z,t) = f(z) I(t)$.

To find the best focus position for the ellipsometer of the invention, it is thus necessary to separate f(z) from I(t). It is mathematically possible to do so, but an undesirably complicated algorithm must be implemented (so that focus speed will almost certainly be compromised).

However, by supplying two measured signals to processor 100 (one signal $F_A(Z,t)$ from photodiode 94A and another signal $F_B(z,t)$ from and photodiode 94B), processor 100 can be programmed to quickly (and efficiently) determine all the useful information of the conventional focus signal f(z). This is accomplished by programming processor 100 to determine the following new focus signal:

$F(z)=F_A(z,t)/F_B(z,t)=f_A(z)/f_B(z)$.

Figure 11:
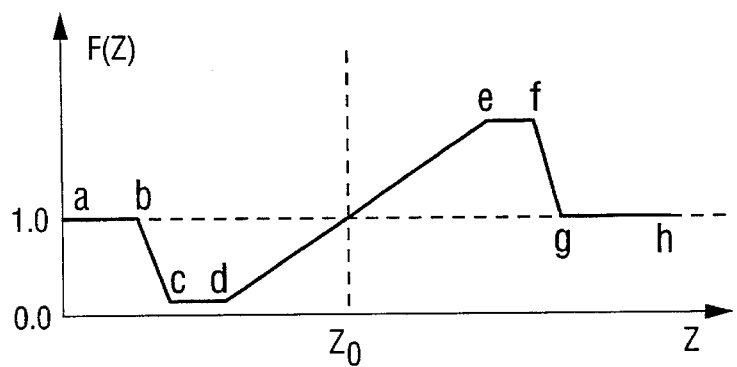
FIG. 11 is a graph of a focus signal, F(z), which is a function of position of sample 3 along the z-axis of FIG. 8. Focus signal F(z) is generated by processing (in processor 98) the two signals measured by detector 94 of FIG. 8.

FIG. 11 is a graph of a typical "new" focus signal F(z) determined from signals $F_A(z,t)$ and $F_B(z,t)$ measured while rotating polarizer 5 and scanning sample 3 along the z-axis. In contrast, FIG. 10 is a graph of a conventional focus signal, f(z), generated using conventional means (i.e., a single photodiode in the position of dual photodiode detector 94) while scanning sample 3 along the z-axis but keeping both polarizer 5 and analyzer 8 fixed.

The shape of F(z) in FIG. 11 can be explained as follows (assuming that sample 3 is scanned from a lowest position "a," through positions "b" through "g," to a highest position "h" along the z-axis of FIG. 8). When sample position z is between "a" and "b", spot 94C is projected onto neither diode 94A nor 94B (so that both diodes produce only a dark current signal, and the ratio of such signals is 1). As the sample position z increases from "b" to "c", the spot 94C sweeps across diode 94B toward 94A (but does not reach diode 94A). Thus, the ratio F(z) has decreasing values less than 1. Then, as the sample position z increases from "c" to "e", the spot 94C sweeps across both diodes 94B and 94A (but continues to sweep upward toward the top of FIG. 9). Thus, the ratio F(z) increases. The ratio F(z) increases to the value F(z)=1, when half of spot 94C is projected on diode 94B and the other half of spot 94C on diode 94A. With the proper optical system configuration, this condition (with sample 3 at the position z=Zo) determines the best focus position. Similarly, the maximum of signal f(z) shown in FIG. 10 can determine the best focus position (but only in the special case, not encountered during normal ellipsometer operation, that both analyzer 8 and polarizer 5 are stationary).

As the sample position z increases from "e" to "g", spot 94C sweeps across diode 94A (but not diode 94B), so that the ratio F(z) remains constant or decreases. Finally, as the sample position z increases from "g" to "h", spot 94C is projected onto neither diode 94A nor 94B.

The auto focus system of FIGS. 8–9 (and its method of operation) offers several advantages, including that: it is fast (i.e., processor 100 determines the necessary values very quickly); the algorithm implemented by processor 100 is simple; and it gives directional information (in the following sense). Based on whether F(z) is greater than or less than 1, the operator can tell whether the sample is above or below the best focus position. This is especially useful for whole wafer mapping. If the sample surface and the surface of stage 3 are reasonably flat, processor 100 can be programmed to assume that the best focus position falls along the increasing portion of the curve F(z). Thus, after a first determination of best focus (in which the data needed to produce the FIG. 11 graph are measured), it is no longer necessary to scan the sample position to determine the best focus position for subsequent sample measurements. Instead, processor 100 can determine the best focus position from the instantaneous value of F(z).

In designing the autofocus assembly of the invention, it is important to consider that the image intensity seen by the camera is time-varying, and that the speed at which the video image can be digitized and processed should be sufficiently high to enable autofocus.

The alternative autofocus assembly of FIG. 7 includes source 92 of off-axis illuminating radiation, apertured mirror 93, apertured mirror 90, and camera 91. Apertured mirror 90 has a slit extending through it, and functions as an incidence angle selection element similar to the way apertured plate 6B of FIG. 6 functions as an incidence angle selection element. Indeed mirror 90 can be of identical design as apertured plate 6B (but the planar surface of mirror 90 which faces away from mirror 7 is highly reflective, while the corresponding planar surface of plate 6B need not be highly reflective). A first portion of the radiation from collection mirror 6 passes through the slit in mirror 90, and then reflects from mirror 7 toward analyzer 8 (just as in the FIG. 1 and FIG. 6 embodiments). However, because mirror 90 is tilted at a small angle with respect to folding mirror 7 (and is positioned along the optical path), mirror 90 reflects a second portion of the radiation that it receives from collection mirror 6 toward camera 91 (this second portion does not pass through the slit in mirror 90, and does not propagate to analyzer 8). The radiation reflected from mirror 90 is focused to camera 91, and camera 91 thus observes the position and size of the spot on sample 3.

Signals indicative of the position and size of the spot are supplied from camera 91 to processor 100. In response to these signals, processor 100 generates focus control signals that are used for focusing the sample (e.g., the focus control signals are used for controlling the position of sample stage 63). Where camera 91 is part of focusing and pattern recognition subsystem 80 of FIG. 1, the signals output from camera 91 are used for pattern recognition as well as for the auto focus function described with reference to FIG. 7.

Apertured mirror 93 has an aperture therethrough which allows polarized beam 9 from polarizer 5 to pass unimpeded to mirror 4. Apertured mirror 93 also reflects off-axis illuminating radiation from source 92 toward mirror 4. This off-axis illuminating radiation is reflected to camera 91, where it enables camera 91 to "see" the position of the spot to which beam 9 is focused on the sample (and to enable pattern recognition and auto focus operations).

Figure 12:
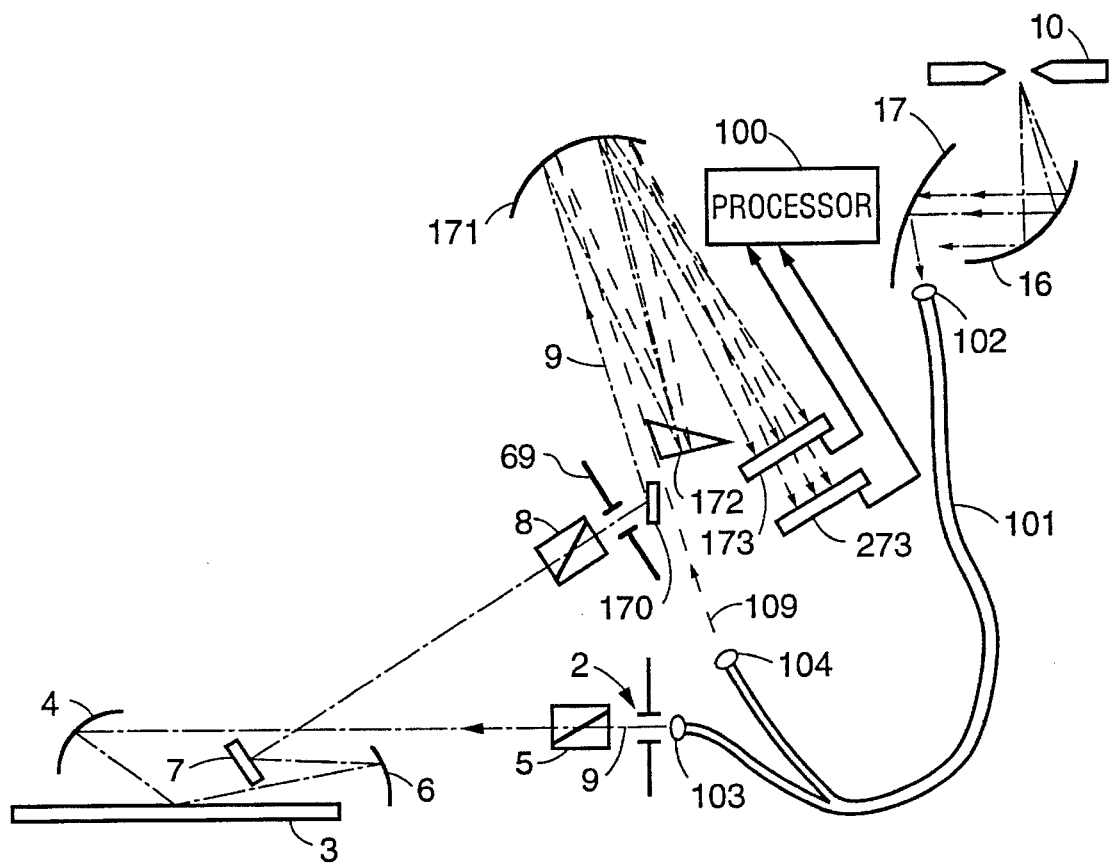
FIG. 12 is a schematic diagram of an alternative embodiment of the inventive ellipsometer (a variation on the system shown in FIG. 1), which detects a reference beam, as well as a sample beam after the sample beam has reflected from a sample. The FIG. 12 system includes a bifurcated optical fiber which emits both the reference beam and sample beam.

Next, with reference to FIG. 12, we describe a class of embodiments in which the inventive ellipsometer includes a reference channel (in addition to a sample channel which detects radiation reflected from the sample). The ellipsometer of FIG. 12 has both a reference channel (including detector 273) and a sample channel (including detector 173). Illuminating radiation from lamp 10 reflects from mirror 16 to mirror 17, and then from mirror 17 to entrance end 102 of bifurcated optical fiber 101. As the radiation propagates within fiber 101 away from end 102, it is split into two portions: a reference beam 109 emitted from end 104 of fiber 101; and sample beam 9 (identical to beam 9 of FIG. 1) emitted from end 103 of fiber 101. Sample beam 9 is polarized in rotating polarizer 5, then is reflectively focused by mirror 4 to sample 3, then reflects from the sample surface to mirror 6 and then mirror 7, and then reflects from mirror 7 through analyzer 8 to the entrance slit in spectrometer entrance slit member 69. In the spectrometer, the portion of sample beam 9 passed through member 69 reflects from mirror 170 to mirror 171, and from mirror 171 to prism 172. The beam components having different wavelengths are refracted in different directions from prism 172 to mirror 171, and from mirror 171 to sample channel detector 173.

Reference beam 109 does not reflect from sample 3, but is directed directly to the spectrometer. Specifically, beam 109 reflects from mirror 171 (i.e., from a slightly different spot on mirror 171 than the spot from which beam 9 reflects) to prism 172. The components of beam 109 having different wavelengths are refracted in different directions from prism 172 to mirror 171, and from mirror 171 to reference channel detector 273. Detectors 173 and 273 are identical, but have slightly offset positions, so that the former receives only radiation of beam 9 reflected from mirror 171, and the latter receives only radiation of beam 109 reflected from mirror 171.

Alternatively, a plate with a double entrance slit is substituted for plate 69 of FIG. 12. In such embodiments, the sample beam passes through one entrance slot into the spectrometer and the reference beam passes through the other entrance slot into the spectrometer.

By processing reference signals from reference channel detector 273 with signals from sample channel detector 173, the thickness (or refractive index) of a thin film on sample 3 can (under some conditions) be more accurately determined than with the FIG. 1 ellipsometer (which has no reference channel). In the In the FIG. 12 system, processor 100 is programmed to normalize the reflectivity measured by sample beam 9 using the reference beam measurements from detector 273, to compensate for such effects as lamp intensity fluctuations and air currents. If such effects are time varying (during the time scale of a single sample measurement) they can affect the measurement unless compensated for by use of a reference channel (such as that of FIG. 12 in which beam 109 propagates to detector 273).

An alternative technique for obtaining a reference beam is to modify the FIG. 1 apparatus so that it splits beam 9 at the location of focus mirror 4. This can be done by designing mirror 4 to have a more complicated shape which focuses a portion of beam 9 (which functions as the sample beam) to sample 3 and directs the remaining portion of beam 9 (the reference beam) directly to collection mirror 6. In this case, the shape of collection mirror 6 would also be modified to reflect the reference beam to a separate channel in the spectrometer, while directing the sample beam to mirror 7 as in FIG. 1.

Variations on the FIG. 1 spectroscopic ellipsometer will include a second optical fiber, identical to fiber 1, for directing the radiation propagating out from analyzer 8 to the spectrometer entrance slit through member 69. Alternatively, the inventive ellipsometer can omit fiber 1, and include only one optical fiber which directs radiation from analyzer 8 to the spectrometer entrance slit.

We have described many embodiments of the inventive spectroscopic ellipsometer. In alternative embodiments of the inventive ellipsometer, polarized radiation having only one wavelength (rather than broadband radiation) is reflected from the sample. These embodiments can include a spectrometer as in FIG. 1, or alternatively a simple photodiode detector which detects the radiation output from the analyzer.

Other embodiments of the invention are not an ellipsometer alone, but a spectrophotometer integrated together with an ellipsometer (preferably any of the above-described spectroscopic ellipsometers) as a single instrument.

In one such preferred embodiment, the FIG. 1 ellipsometer includes above-mentioned movable mirror 7 (and actuator 17A), and the spectrophotometer of FIG. 2 is integrated with the FIG. 1 ellipsometer as a single instrument. To operate such combined instrument as an ellipsometer, actuator 17A moves mirror 17 to the position shown in FIG. 1, in which mirror 17 reflects beam 12 from mirror 16 to fiber 1. To operate the combined instrument as a spectrophotometer, actuator 17A moves mirror 17 to a second position (not shown in FIG. 1) outside the optical path of beam 12 in which mirror 17 does not impede propagation of beam 12 from mirror 16 to lens 32 and mirror 22 of the FIG. 2 spectrophotometer.

In another such embodiment, the FIG. 1 ellipsometer includes above-mentioned movable mirror 7 (and actuator 17A), the FIG. 2 spectrophotometer is integrated with the FIG. 1 ellipsometer as a single instrument, and both the spectrophotometer and ellipsometer operate simultaneously. This is accomplished by substituting apertured paraboloid mirror 17B (of FIG. 3, which has an aperture therethrough) for mirror 17. Mirror 17B splits the radiation from lamp 10 into two portions: one portion which reflects from mirror 16 to mirror 17B, and from the surface of mirror 17B (which surrounds the aperture) to fiber 1; and a second portion which propagates from mirror 16 through the aperture in mirror 17B to filter 18 of FIG. 2.

FIG. 2 shows a preferred spectrophotometer useful with (or as a selectable alternative to) the inventive ellipsometer in a combined ellipsometer/spectrophotometer instrument. The FIG. 2 apparatus separately detects both UV and visible radiation reflected from a small spot on sample 3, and includes processor 100 (which is also shown in FIG. 1, and is shared with the FIG. 1 apparatus when FIGS. 1 and 2 are combined in one instrument). The apparatus shown in FIG. 2 is described in detail in U.S. Ser. No. 07/899,666, filed Jun. 16, 1992 (abstract published on Apr. 26, 1994 as the abstract of U.S. Pat. No. 5,306,916), and such description is incorporated herein by reference.

FIG. 2 includes a broadband small spot spectral reflectometer, camera, and autofocus apparatus, and its optical system measures reflectance of sample 3. Sample stage 63 is provided for moving sample 3 with respect to the optical system. The optical system includes illumination, reflectometer viewing, and autofocus subsystems, and any given optical element may be part of more than one of these subsystems.

When the FIG. 2 apparatus is integrated with the ellipsometer of the invention, its illumination subsystem shares the following components with the ellipsometer (e.g., the FIG. 1 apparatus): lamp 10 which emits broadband beam comprising visible and UV radiation; lamp housing window 14; off-axis paraboloid mirror 16; UV cutoff filter 18 and color filter 20; and processor 100. Reflective objective 40 shown in FIG. 1 (and FIG. 2) is not part of the ellipsometer of FIG. 1. All these elements have been described above with reference to FIG. 1, and objective 40 will be described in more detail below. It will be appreciated that when FIG. 2 is integrated with the FIG. 1 apparatus (or another ellipsometer), processor 100 which they share is programmed to process signals received from each detector of the ellipsometer (e.g. detector 173 of FIG. 1) as well as signals received from elements 72, 74, and 90 of FIG. 2.

The FIG. 2 apparatus also includes flip-in UV cutoff filter 18, color filter 20 (which is typically one of several filters mounted on a wheel), flat mirror 22, concave mirror 24, aperture mirror 28 with flip-in forty-micron fine focus aperture 30, large achromat 32, field illumination shutter 31, fold mirror 36, and small achromat 38.

The illumination system provides both measurement beam 25 and field illumination beam 34 to beam divider 45. Off-axis paraboloid mirror 16 collimates beam 12 from lamp 10, and the beam is then optionally filtered by flip-in UV cutoff filter 18 and color filter wheel 20. UV cutoff filter 18 is used in part to limit the spectrum of beam 12 so that when beam 12 is dispersed by a diffraction grating, the first and second order diffraction beams do not overlap. Part of beam 12 is reflected by flat mirror 22 onto concave mirror 24 to form measurement beam 25.

Field illumination beam 34, another part of beam 12, is focused by large achromat 32, so that fold mirror 36 reflects an image of lamp 10 toward small achromat 38. Small achromat 38 collects the radiation in beam 34 before it reflects from aperture mirror 28. Aperture mirror 28 is preferably a fused silica plate with a reflective coating on one side, with a 150 micron square etched from the reflective coating to provide an aperture for beam 25. The aperture is placed at one conjugate of objective 40. The field illumination can be turned off by placing field illumination shutter 31 in the optical path of field illumination beam 34.

Narrow measurement beam 25 and wide field illumination beam 34 are rejoined at aperture mirror 28, with field illumination beam 34 reflecting off the front of aperture mirror 28, and measurement beam 25 passing through the aperture.

The reflectometer, viewing, and autofocus subsystems of FIG. 2 include objective 40, beamsplitter mirror 45, sample beam 46, reference beam 48, concave mirror 50, flat mirror 43, reference plate 52 with a reference spectrometer pinhole therethrough, sample plate 54 with a sample spectrometer pinhole therethrough, second fold mirror 68, diffraction grating 70, sample linear photodiode array 72, reference linear photodiode array 74, reference photodiode 95, sample photodiode 93, an achromat with a short focal length and a right angle prism (not shown), beamsplitter cube 84, penta prism 86, achromats 88 and 90 with long focal lengths, achromat 80', third fold mirror 89, focus detector 98, neutral density filter wheel 97, fourth fold mirror 91, and video camera 96. These elements are preferred for implementing the pattern recognition means of subsystem 80 shown in FIG. 1.

Objective 40 is preferably a reflective objective (as shown in FIG. 2), and preferably has several selectable magnifications. In one embodiment, objective 40 includes a 15× Schwarzchild design all-reflective objective, a 4× Nikon CFN Plan Apochromat (color corrected at three wavelengths), and a 1× UV transmissive objective, all mounted on a rotatable turret which allows for one of the three objectives to be placed in the optical path of sample beam 46.

The FIG. 2 system operates as follows to measure a relative reflectance spectrum for sample 3 (which is assumed to be a semiconductor wafer in the following description). Shutter 31 is placed in the path of field illumination beam 34, so that the "combined" beam incident at beamsplitter mirror 45 consists only of measurement beam 25. Beamsplitter mirror 45 deflects a portion of beam 25 toward objective 40, thus forming sample beam 46. Reference beam 48 is an undeflected portion of beam 25 which propagates past (not through) beamsplitting mirror 45. Because sample beam 46 and reference beam 48 are derived from the same source (lamp 10) and because beam 25 is radially uniform, reference beam 48 and sample beam 46 have proportionally dependent spectral intensities. Also, since beamsplitter mirror 45 is a totally reflecting mirror in half of an optical path rather than a partially reflecting mirror in the entire optical path, a continuous broadband spectrum is reflected with good brightness.

Reference beam 48 does not initially interact with beamsplitter mirror 45, but instead illuminates concave mirror 50. Concave mirror 50 is slightly off-axis, so reference beam 48 is reflected onto the reverse face of beamsplitter mirror 45, and flat mirror 43 re-reflects reference beam 48 into alignment with the reference spectrometer pinhole through plate 52. Flat mirror 43 realigns reference beam 48 with sample beam 46 so that both beams pass through their respective spectrometer pinholes substantially parallel.

The focal length of concave mirror 50 is such that reference beam 48 is in focus at the reference spectrometer pinhole (which extends through plate 52). The radiation passing through the reference spectrometer pinhole and reflecting from fold mirror 68 is dispersed by diffraction grating 70. The resulting first order diffraction beam is collected by reference linear photodiode array 74, thereby measuring a reference reflectance spectrum.

Sample beam 46 is reflected from beamsplitter mirror 45 towards objective 40, which focuses sample beam 46 onto wafer 3, and the reflected sample beam 46 is focused by objective 40 onto the sample spectrometer pinhole (which extends through plate 54). The reflected sample beam 46 does not interact with beamsplitter mirror 45 on the reflected path, because sample beam 46 passed through the space behind beamsplitter mirror 45, through which reference beam 48 also passes. The radiation passing through the sample spectrometer pinhole and reflecting from fold mirror 68 is dispersed by diffraction grating 70. As with the reference beam, the resulting first order diffraction beam of the sample beam is collected by sample linear photodiode array 72, thereby measuring the sample spectrum.

The relative reflectance spectrum can be simply obtained by processing the outputs of arrays 72 and 74 in processor 100, by dividing the sample light intensity at each wavelength (the output of array 72) by the reference intensity at each wavelength (the output of array 74). Typically, this involves 512 division computations, in cases in which each of arrays 72 and 74 is a 512-diode linear photodiode array. A typical relative reflectance spectrum will include components ranging from 220 nm to 830 nm.

In some embodiments, diffraction grating 70 is a concave holographic grating and the spectrometer pinholes (through plates 52 and 54) are 15 mm apart. This embodiment of diffraction grating 70 is holographically corrected to image multiple spectra, since the 15 mm spacing does not allow for both beams to be centered on the grating. One such grating is a multiple spectra imaging grating supplied by Instruments SA. It is also desirable that grating 70 be designed so that the angle of detectors 72 and 74 causes reflections from the detectors to propagate away from the grating.

The FIG. 2 system includes an autofocus subsystem having a coarse-focus mode to allow for wide range lock-in, and a fine-focus mode for use once a coarse focus is achieved. In the coarse-focus mode, flip-in fine-focus aperture 30 is flipped out of the optical path, and the square aperture of aperture mirror 28 is imaged onto detector 98.

Detector 98 has a position output, which is dependent on the position of the centroid of the radiation falling on detector 98, and an intensity output, which is dependent on the incident intensity at detector 98. Detector 98 is positioned to avoid dark regions of the out-of-focus image. In the coarse-focus mode, the centroid of the image falling on detector 98 indicates not only the direction in which focus lies, but also how far out of focus wafer 3 is. The Z position of wafer 3 (the separation between wafer 3 and objective 40) is then adjusted until the centroid of the light falling on detector 98 is centered near the center of detector 98. With the appropriate positioning and feedback mechanism, wafer 3 can be kept in coarse focus while the wafer is being moved in the X and Y directions.

For fine focus, flip-in aperture member 30 is flipped into the optical path of measurement beam 25, resulting in a smaller square image reaching detector 98. The smaller square image has a size of about 40 microns with an 1X objective. Since aperture member 30 has an aperture the same size as the aperture through plate 54, and since the two apertures are at conjugates of objective 40, when wafer 3 is in focus, very little radiation strikes plate 54 (away from the aperture through plate 54) to be reflected onto detector 98.

Thus in the fine-focus mode, the intensity output of detector 98 is used to bring wafer 3 into focus, with the Z position of wafer 3 being adjusted until the intensity output of detector 98 is minimized.

There are several other hardware features important to a preferred implementation of the FIG. 2 system. One important feature is that the 1× and 15× pupil stops (of objective 40) should be oriented to increase the insensitivity of the FIG. 2 system to ripple on the surface of sample 3 (e.g., micro ripple in the thickness of a thin film coating on sample 3) system), in the manner described in U.S. Ser. No. 07/899,666, filed Jun. 16, 1992 (abstract published on Apr. 26, 1994 as the abstract of U.S. Pat. No. 5,306,916).

Another feature is that lamp housing window 14 should be very thin to reduce chromatic aberration in the measurement illumination path. This chromatic aberration causes the UV and visible images of the arc of lamp 10 projected onto aperture mirror 28 to separate, creating problems with the 15× focus curve.

Another feature is that means for adjusting the lamp housing's position along the z-axis shown in FIG. 2 should hold the lamp very steadily. If the lamp position drifts while measuring a wafer, the ratio of UV to visible radiation changes and the measurements may drift.

The autofocus subsystem of FIG. 2 uses the image reflected from sample plate 54. Sample plate 54 is preferably a reflective fused silica plate with an aperture therethrough. For simplicity, an identical reflective fused silica plate with an aperture is used as reference plate 52, however reference plate 52 need not be reflecting.

The image reflected from sample plate 54 is also used for viewing wafer 3. As shown in FIG. 2, sample beam 46 is partially reflected off sample plate 54, through short focal length achromat 80', and reflects from mirror 89 into beamsplitter cube 84. Beamsplitter cube 84 splits the incoming beam into a camera beam 65 and a focus beam 63'. Camera beam 65 is then reflected in penta prism 86, focused by long focal length achromat 90, filtered by N.D. filter 97, and reflected into video camera 96 by fold mirror 91. Penta prism 86 is used instead of a mirror, so that the image received by video camera 96 is a non-inverted image of wafer 3.

As shown in FIG. 2, long focal length achromat 88 directs beam 63' onto detector 98. In an alternative embodiment (not shown), where less space is available, long focal length achromat 88 is replaced by a medium focal length achromat and a negative lens such as a barlow lens.

Beamsplitter cube 84 is positioned slightly off-axis so that unwanted reflections from the faces of beamsplitter cube 84 are skewed out of the optical path of the entering beam. This is accomplished by rotating the beamsplitter cube 1° to 10°, preferably 3° to 5°, about an axis normal to the reflection surface within the cube. Similarly, penta prism 86 is rotated in the plane of reflection to remove unwanted reflections from the field of view. Additionally, to capture stray radiation from unwanted internal reflections within beamsplitter cube 84, black glass is glued to the unused surfaces of beamsplitter cube 84. In this way, only the desired internal reflection of beam 65 and beam 63' exit beamsplitter cube 84.

FIG. 14 is a schematic diagram of a preferred embodiment of the invention which is a spectrophotometer integrated together with a spectroscopic ellipsometer as a single instrument. All components of FIG. 14 that are identified by the same reference numerals as corresponding elements of FIGS. 1 and 2 are identical to such corresponding elements, and the description thereof will not be repeated below. The elements of FIG. 14 that do not comprise the ellipsometer differ (i.e., the non-ellipsometer portion of FIG. 14 differs) from the FIG. 2 system in that elements 255, 257, 254, 256, 90, 153, 252, and 158 of FIG. 2 are omitted. The reason these elements are omitted from the "combined" instrument of FIG. 14 is that the ellipsometer subsystem of FIG. 14 is capable of determining most (or all) of the sample characteristics that the omitted elements could have determined. The FIG. 14 spectrophotometer shares arc lamp 10, paraboloid mirror 16, filters 18 and 20, sample stage 63, and processor 100 with the ellipsometer subsystem. By controlling the position of mirror 17 (e.g., using actuator 17A of FIG. 1), radiation from lamp 10 can be directed to sample 3 from either elements 1, 5, and 4 of the ellipsometer subsystem, or from elements 32, 36, 38, 28, 30, 45, and 40 of the spectrophotometer subsystem.

Several embodiments of optical systems according to the present invention have been described. The description is illustrative and not restrictive. Many other variations on the invention will become apparent to those of skill in the art upon review of this disclosure. Merely by way of example, the sample measured by the invention need not be a wafer, but can be any other reflective object; and fold mirrors can be removed where space allows, and additional fold mirrors can be provided where space is limited. The scope of the invention should be determined not merely with reference to the above description, but should be determined with reference to the appended claims along with their full scope of equivalents.

What is claimed is:

1. A spectroscopic ellipsometer for measuring a sample, including:

a source which emits broadband radiation;

a polarizer for polarizing the broadband radiation, thereby producing a sample beam;

an analyzer positioned for receiving radiation of the sample beam that has reflected from the sample, wherein the analyzer produces an output beam in response to said radiation;

a detector for converting the output beam into a detector output, said detector output having a polarization state; and all-reflective optics between the polarizer and the analyzer, wherein the sample beam reflects with low incidence angle from each component of the all-reflective optics, and wherein the all-reflective optics reflectively focuses the sample beam to a small spot on the sample, each said low incidence angle being no more than 30 degrees from a normal direction to a component; and means for processing the detector output to determine amplitude and phase changes of the output beam polarization state caused by reflection by the sample.

2. The ellipsometer of claim 1, wherein the all-reflective optics reflectively focuses the sample beam to the spot at a high incidence angle.

3. The ellipsometer of claim 1, wherein the all-reflective optics reflectively focuses the sample beam to the spot at a range of high incidence angles.

4. The ellipsometer of claim 3, wherein the range of high incidence angles is a substantial range of high incidence angles, and also including:

an incidence angle selection element for selecting, for measurement by the detector means, only radiation reflected from the sample at a subrange of said substantial range of high incidence angles.

5. The ellipsometer of claim 4, wherein the incidence angle selection element is an apertured plate with a slit therethrough.

6. The ellipsometer of claim 5, wherein the apertured plate is movably mounted with respect to the optical path of said radiation reflected from the sample, and also including:

actuator means for moving the apertured plate to a position at which the slit determines said subrange of said substantial range of high incidence angles.

7. The ellipsometer of claim 1, wherein the all-reflective optics reflectively focuses the sample beam to a small, compact spot on the sample.

8. The ellipsometer of claim 7, also including:

an apertured entrance element positioned between the source and the polarizer, said entrance element including an elongated entrance slit for passing a beam of said broadband radiation to the polarizer, wherein each of the beam and the sample beam has an elongated cross-section, and wherein the all-reflective optics includes means for reflectively focusing the sample beam to a small, substantially square spot on the sample.

9. The ellipsometer of claim 7, wherein the sample beam has an elongated cross-section, and wherein the all-reflective optics includes an elliptical focusing mirror which reflectively focuses the sample beam to a small, substantially square spot on the sample.

10. The ellipsometer of claim 1, wherein the detector means is a spectrometer, and wherein the spectrometer includes photosensitive means for measuring intensity of said output beam at each of a number of different wavelength ranges.

11. The ellipsometer of claim 10, wherein the photosensitive means is an intensified photodiode array.

12. The ellipsometer of claim 1, wherein the polarizer is a minimal-length Rochon prism.

13. The ellipsometer of claim 12, wherein the minimal-length Rochon prism is rotatably mounted for rotation about the optical path.

14. The ellipsometer of claim 1, also including:

an apertured entrance element positioned between the source and the polarizer, said entrance element including an entrance slit for passing a beam of said broadband radiation to the polarizer; and an optical fiber positioned between the source and the entrance element for directing said broadband radiation to the entrance element.

15. The ellipsometer of claim 1, also including:

reference channel means for diverting a reference portion of the broadband radiation from the source directly to the detector means in such a manner that said reference portion does not reflect from the sample.

16. The ellipsometer of claim 15, wherein the detector means includes:

first photodiode array means for measuring the output beam; and second photodiode array means for measuring said reference portion.

17. The ellipsometer of claim 15, wherein the reference channel means includes a bifurcated optical fiber having an inlet end positioned for receiving the broadband radiation, a first outlet end for directing a sample portion of the broadband radiation to the polarizer, and a second outlet end for directing the reference portion directly to the detector means.

18. The ellipsometer of claim 1, also including:

sample stage means for supporting the sample and moving the sample relative to the all-reflective optics; and an autofocus assembly for measuring a focus signal indicative of radiation reflected from a spot on the sample during movement of the sample stage means with the sample supported thereon, whereby a best focus position of the all-reflective optics relative to the sample can be determined from the focus signal.

19. The ellipsometer of claim 18, wherein the autofocus assembly includes:

a dual photodiode detector, which receives a substantially focused image of the spot.

20. The ellipsometer of claim 19, also including:

a beamsplitting mirror positioned for diverting said radiation reflected from a spot on the sample during movement of the sample stage means to the dual photodiode detector.

21. The ellipsometer of claim 20, wherein the dual photodiode detector includes a first photodiode which outputs a first intensity signal and a second photodiode which outputs a second intensity signal, and wherein the autofocus assembly also includes:

a processor which receives the first intensity signal and the second intensity signal, wherein the processor is programmed to process the first intensity signal and the second intensity signal to generate a focus signal indicative of said best focus position.

22. The ellipsometer of claim 18, wherein the autofocus assembly includes:

camera means; and an apertured mirror positioned along the optical path between the all-reflective optics and analyzer, for reflecting said radiation reflected from a spot on the sample during movement of the sample stage means to the camera means.

23. The ellipsometer of claim 1, wherein the broadband radiation includes UV radiation but not visible radiation.

24. The ellipsometer of claim 1, wherein the broadband radiation includes UV, visible, and near infrared radiation.

25. A method for performing spectroscopic ellipsometry measurements on a sample, including the steps of:

(a) polarizing the broadband radiation, thereby producing a sample beam;

(b) reflectively focusing the sample beam to a small spot on the sample using all-reflective optics in such a manner that the sample beam reflects with an angle from each component of the all-reflective optics of not more than 30 degrees from a normal direction to each such component;

(c) analyzing radiation of the sample beam that has reflected from the sample, thereby producing an output beam, said output beam having a polarization state; and (d) detecting the output beam to determine amplitude and phase changes of the output beam polarization state caused by reflection by the sample.

26. The method of claim 25, wherein step (b) includes the step of reflectively focusing the sample beam to the spot at a high incidence angle.

27. The method of claim 25, wherein step (b) includes the step of reflectively focusing the sample beam to the spot at a range of high incidence angles.

28. The method of claim 27, wherein the range of high incidence angles is a substantial range of high incidence angles, and also including the step of:

(e) selecting, for detection, only radiation reflected from the sample at a subrange of said substantial range of high incidence angles.

29. The method of claim 28, wherein said subrange is a narrow range of angles.

30. The method of claim 28, wherein the substantial range of high incidence angles is the range from about 63.5 degrees to about 80.5 degrees, and the subrange is a narrow range of angles centered at Brewster's angle for the sample.

31. The method of claim 28, wherein step (e) includes the step of:

moving an apertured plate having an elongated slit therethrough to a position at which the slit determines said subrange of said substantial range of high incidence angles.

32. The method of claim 25, wherein step (b) includes the step of reflectively focusing the sample beam to a small, compact spot on the sample.

33. The method of claim 32, wherein the sample beam has an elongated cross-section, and wherein the small, compact spot is a small, substantially square spot.

34. The method of claim 25, wherein the sample beam has an elongated cross-section, and wherein step (b) includes the step of reflectively focusing the sample beam from an elliptical focusing mirror to a small, substantially square spot on the sample.

35. The method of claim 25, wherein step (d) includes the step of directing the output beam to an intensified photodiode array, thereby measuring intensity of said output beam at each of a number of different wavelength ranges.

36. The method of claim 25, wherein step (a) includes the step of rotating a minimal-length Rochon prism.

37. The method of claim 25, also including the step of:

diverting a reference portion of the broadband radiation directly to a detector means in such a manner that said reference portion does not reflect from the sample.

38. The method of claim 25, also including the steps of:

supporting the sample on a sample stage means and moving the sample and sample stage means relative to the all-reflective optics; and measuring a focus signal indicative of radiation reflected from a spot on the sample during movement of the sample stage means and the sample, whereby a best focus position of the all-reflective optics relative to the sample can be determined from the focus signal.

39. An optical instrument, including a spectrophotometer and an ellipsometer integrated together as a single instrument with the spectrophotometer, said instrument including:

radiation source means which emits radiation; and means for directing a first portion of the radiation to the spectrophotometer and a second portion of the radiation to the ellipsometer, wherein the spectrophotometer and the ellipsometer simultaneously focus the radiation received thereby to a single spot on a sample, and wherein the ellipsometer includes:

a polarizer for polarizing the radiation, thereby producing a sample beam;

an analyzer positioned for receiving radiation of the sample beam that has reflected from the sample, wherein the analyzer produces an output beam in response to said radiation, said output beam having a polarization state;

detector means for detecting the output beam to determine amplitude and phase changes of the output beam polarization state caused by reflection by the sample;

all-reflective optics between the polarizer and the analyzer, wherein the sample beam reflects with an angle from each component of the all-reflective optics of not more than 30 degrees from a normal direction to each such component, and wherein the all-reflective optics reflectively focuses the sample beam to the spot on the sample.

40. The optical instrument of claim 39, wherein the radiation source means is a lamp shared by the spectrophotometer and the ellipsometer.

41. The optical instrument of claim 39, wherein the spot is a small, compact spot.

42. The optical instrument of claim 39, wherein the radiation is broadband radiation.

43. The optical instrument of claim 39, wherein the ellipsometer also includes:

an incidence angle selection element for selecting, for measurement by the detector means, only radiation reflected from the sample at a subrange of said substantial range of high incidence angles, wherein the incidence angle selection element is an apertured plate with a slit therethrough.

44. An optical instrument, including a spectrophotometer and an ellipsometer integrated together as a single instrument with the spectrophotometer, said instrument including:

radiation source means which emits radiation; and beam diverting means for directing the radiation to a selected one of the spectrophotometer and the ellipsometer, to enable only said selected one of the spectrophotometer and the ellipsometer to focus said radiation received from the beam diverting means to a spot on a sample, wherein the ellipsometer includes:

a polarizer for polarizing the radiation, thereby producing a sample beam;

an analyzer positioned for receiving radiation of the sample beam that has reflected from the sample, wherein the analyzer produces an output beam in response to said radiation, said output beam having a polarization state;

detector means for detecting the output beam to determine amplitude and phase changes of the output beam polarization state caused by reflection by the sample;

all-reflective optics between the polarizer and the analyzer, wherein the sample beam reflects with an angle from each component of the all-reflective optics of not more than 30 degrees from a normal direction to each such component, and wherein the all-reflective optics reflectively focuses the sample beam to the spot on the sample at a substantial range of high incidence angles.

45. The optical instrument of claim 44, wherein the radiation source means is a single lamp.

46. The optical instrument of claim 44, wherein the radiation is broadband radiation.

47. The optical instrument of claim 44, wherein the beam diverting means includes:

a movably mounted mirror; and an actuator for moving the mirror to a selected one of a first position in which said mirror reflects the radiation to the ellipsometer, and a second position in which said mirror allows the radiation to propagate to the spectrophotometer.

48. The optical instrument of claim 44, wherein the ellipsometer also includes:

an incidence angle selection element for selecting, for measurement by the detector means, only radiation reflected from the sample at a subrange of said substantial range of high incidence angles, wherein the incidence angle selection element determines a slit-shaped region and all radiation selected by the incidence angle selection element for measurement by the detector means propagates away from the slit-shaped region after incidence at the incidence angle selection element.

49. The optical instrument of claim 48, wherein the incidence angle selection element is an apertured plate with a slit therethrough.

50. A spectroscopic ellipsometer for measuring a sample, including:

a source which emits broadband radiation;

a polarizer for polarizing the broadband radiation, thereby producing a sample beam;

an analyzer positioned for receiving radiation of the sample beam that has reflected from the sample, wherein the analyzer produces an output beam in response to said radiation, said output beam having a polarization state;

detector means for detecting the output beam to determine amplitude and phase changes of the output beam polarization state caused by reflection by the sample;

all-reflective optics between the polarizer and the analyzer, wherein the sample beam reflects with an angle from each component of the all-reflective optics of not more than 30 degrees from a normal direction to each such component, and wherein the all-reflective optics reflectively focuses the sample beam to a spot on the sample;

sample stage means for supporting the sample and moving the sample relative to the all-reflective optics; and an autofocus assembly for measuring a focus signal indicative of radiation reflected from the spot on the sample during movement of the sample stage means with the sample supported thereon, whereby a best focus position of the all-reflective optics relative to the sample can be determined from the focus signal, wherein the autofocus assembly consists of:

a dual photodiode detector, which receives a substantially focused image of the spot, wherein the dual photodiode detector includes a first photodiode which outputs a first intensity signal and a second photodiode which outputs a second intensity signal; and a processor which receives the first intensity signal and the second intensity signal, wherein the processor is programmed to process the first intensity signal and the second intensity signal to generate a focus signal indicative of said best focus position.

51. The ellipsometer of claim 50, also including:

a beamsplitting mirror positioned for diverting said radiation reflected from the spot on the sample during movement of the sample stage means to the dual photodiode detector.

52. A spectroscopic ellipsometer for measuring a sample, including:

a source which emits broadband radiation;

a polarizer for polarizing the broadband radiation, thereby producing a sample beam;

an analyzer positioned for receiving radiation of the sample beam that has reflected from the sample, wherein the analyzer produces an output beam in response to said radiation, said output beam having a polarization state;

detector means for detecting the output beam to determine amplitude and phase changes of the output beam polarization state caused by reflection by the sample;

all-reflective optics between the polarizer and the analyzer, wherein the sample beam reflects with an angle from each component of the all-reflective optics of not more than 30 degrees from a normal direction to each such component, and wherein the all-reflective optics reflectively focuses the sample beam to a spot on the sample at a substantial range of high incidence angles; and an incidence angle selection element for selecting, for measurement by the detector means, only radiation reflected from the sample at a subrange of said substantial range of high incidence angles, wherein the incidence angle selection element determines a slit-shaped region and all radiation selected by the incidence angle selection element for measurement by the detector means propagates away from the slit-shaped region after incidence at the incidence angle selection element.

53. The ellipsometer of claim 52, wherein said subrange is a single, selected angle.

54. The ellipsometer of claim 52, wherein said subrange is a narrow range of angles.

55. The ellipsometer of claim 52, wherein the substantial range of high incidence angles is the range from about 63.5 degrees to about 80.5 degrees, and the subrange is a narrow range of angles centered at Brewster's angle for the sample.

56. The ellipsometer of claim 52, wherein said subrange is a single, selected angle.

57. The ellipsometer of claim 52, wherein said subrange is a narrow range of angles.

58. The ellipsometer of claim 52, wherein the substantial range of high incidence angles is the range from about 63.5 degrees to about 80.5 degrees, and the subrange is a narrow range of angles centered at Brewster's angle for the sample.

59. The ellipsometer of claim 52, wherein the incidence angle selection element is an apertured plate with a slit therethrough.

60. The ellipsometer of claim 59, wherein the apertured plate is movably mounted with respect to the optical path of said radiation reflected from the sample, and also including:

actuator means for moving the apertured plate to a position at which the slit determines said subrange of said substantial range of high incidence angles.

61. The ellipsometer of claim 52, wherein the all-reflective optics reflectively focuses the sample beam to a small, compact spot on the sample.

62. The ellipsometer of claim 61, also including:

an apertured entrance element positioned between the source and the polarizer, said entrance element including an elongated entrance slit for passing a beam of said broadband radiation to the polarizer, wherein each of the beam and the sample beam has an elongated cross-section, and wherein the all-reflective optics includes means for reflectively focusing the sample beam to a small, substantially square spot on the sample.

63. The ellipsometer of claim 52, wherein the detector means is a spectrometer, and wherein the spectrometer includes photosensitive means for measuring intensity of said output beam at each of a number of different wavelength ranges.

64. The ellipsometer of claim 63, wherein the photosensitive means is an intensified photodiode array.

65. The ellipsometer of claim 52, also including:

an apertured entrance element positioned between the source and the polarizer, said entrance element including an entrance slit for passing a beam of said broadband radiation to the polarizer; and an optical fiber positioned between the source and the entrance element for directing said broadband radiation to the entrance element.

66. A method of performing spectroscopic ellipsometry measurements on a sample, including the steps of:

(a) polarizing broadband radiation, thereby producing a sample beam;

(b) reflectively focusing the sample beam to a spot on the sample using all-reflective optics at a substantial range of high incidence angles so that the sample beam reflects from each component of the all-reflective optics with an angle of not more than 30 degrees from the normal direction of each such component;

(c) selecting, for detection, only radiation reflected from the sample at a subrange of the substantial range of high incidence angles, by positioning an incidence angle selection element in the path of radiation of radiation of the sample beam that has reflected from the sample, where the incidence angle selection element determines a slit-shaped region and all radiation selected by the incidence angle selection element for detection propagates away from the slit-shaped region following incidence at the incidence angle selection element;

(d) analyzing radiation of the sample beam that has reflected from the sample, thereby producing an output beam; and (e) detecting radiation of the output beam that has been analyzed in step (d) and has been selected by the incidence angle selection element during step (c).

67. The method of claim 66, wherein said subrange is a narrow range of angles.

68. The method of claim 66, wherein the substantial range of high incidence angles is the range from about 63.5 degrees to about 80.5 degrees, and the subrange is a narrow range of angles centered at Brewster's angle for the sample.

69. The method of claim 66, wherein step (c) includes the step of:

moving an apertured plate having an elongated slit therethrough to a position at which the slit determines said subrange of said substantial range of high incidence angles.

70. The method of claim 66, wherein step (b) includes the step of reflectively focusing the sample beam to a small, compact spot on the sample.

71. The method of claim 70, wherein the sample beam has an elongated cross-section, and wherein the small, compact spot is a small, substantially square spot.

72. The method of claim 66, wherein the sample beam has an elongated cross-section, and wherein step (b) includes the step of reflectively focusing the sample beam from an elliptical focusing mirror to a small, substantially square spot on the sample.

* * * * *

US005608526C1

(12) EX PARTE REEXAMINATION CERTIFICATE (5211th)
United States Patent
Piwonka-Corle et al.

(10) Number: US 5,608,526 C1
(45) Certificate Issued: Oct. 4, 2005

(54) FOCUSED BEAM SPECTROSCOPIC ELLIPSOMETRY METHOD AND SYSTEM

(75) Inventors: Timothy R. Piwonka-Corle, Portland, OR (US); Karen F. Scoffone, Redwood City, CA (US); Xing Chen, San Jose, CA (US); Lloyd J. Lacomb, Jr., Santa Clara, CA (US); Jean-Louis Stehle, Colombes (FR); Dorian Zahorski, Vanves (FR); Jean-Pierre Rey, Fontenay aux Roses (FR)

(73) Assignee: Tencor Instruments, Santa Clara, CA (US)

Reexamination Request:
No. 90/006,309, Jun. 14, 2002

Reexamination Certificate for:
Patent No.: 5,608,526
Issued: Mar. 4, 1997
Appl. No.: 08/375,353
Filed: Jan. 19, 1995

(51) Int. Cl.[7] ............................................. G01N 21/21
(52) U.S. Cl. ......................................................... 356/369
(58) Field of Search ................................. 356/364, 365, 356/366, 367, 368, 369, 630–632; 250/225

(56) References Cited

U.S. PATENT DOCUMENTS 3,874,797 A 4/1975 Kasai
4,210,401 A 7/1980 Batten (Continued)

FOREIGN PATENT DOCUMENTS

EP 0652415 A1 5/1995
FR 2602338 A 2/1988

(Continued)

OTHER PUBLICATIONS

"Characterization of growing thin films by in situ ellipsometry, spectral reflectance and transmittance measurements, and ion–scattering spectroscopy", R.P. Netterfield, et al., *Rev. Sci. Instrum.* vol. 56 (11), Nov. 1985, pp. 1995–2003.

(Continued)

*Primary Examiner*—Hoa Q. Pham

(57) ABSTRACT

A method and system for spectroscopic ellipsometry employing reflective optics to measure a small region of a sample by reflecting radiation (preferably broadband UV, visible, and near infrared radiation) from the region. The system preferably has an autofocus assembly and a processor programmed to determine from the measurements the thickness and/or complex refractive index of a thin film on the sample. Preferably, only reflective optics are employed along the optical path between the polarizer and analyzer, a sample beam reflects with low incidence angle from each component of the reflective optics, the beam is reflectively focused to a small, compact spot on the sample at a range of high incidence angles, and an incidence angle selection element is provided for selecting for measurement only radiation reflected from the sample at a single, selected angle (or narrow range of angles). The focusing mirror preferably has an elliptical shape, to reduce off-axis aberrations in the focused beam. Some embodiments include both a spectrophotometer and an ellipsometer integrated together as a single instrument. In such instrument, the spectrophotometer and ellipsometer share a radiation source, and radiation from the source can be focused by either the spectrophotometer or the ellipsometer to the same focal point on a sample. Preferred embodiments of the ellipsometer employ a rotating, minimal-length Rochon prism as a polarizer, and include a spectrometer with an intensified photodiode array to measure reflected radiation from the sample, and a reference channel (in addition to a sample channel which detects radiation reflected from the sample).

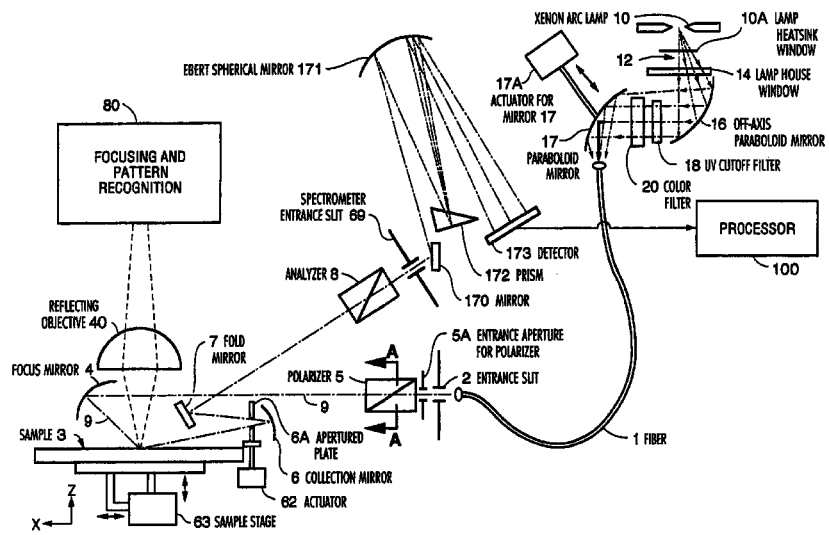

U.S. PATENT DOCUMENTS

| | | |
|---|---|---|
| 4,645,349 A | 2/1987 | Tabata |
| 4,653,908 A | 3/1987 | Yajima et al. |
| 4,653,924 A | 3/1987 | Itonaga et al. |
| 4,655,595 A | 4/1987 | Bjork et al. |
| 4,672,196 A | 6/1987 | Canino |
| 4,692,024 A | 9/1987 | Bloss |
| 4,790,659 A | 12/1988 | Erman et al. |
| 4,810,872 A | 3/1989 | Murakoshi et al. |
| 4,834,539 A | 5/1989 | Le Bris et al. |
| 4,865,445 A | 9/1989 | Kuriyama et al. |
| 4,957,368 A | 9/1990 | Smith |
| 4,999,014 A | 3/1991 | Gold et al. |
| 5,042,951 A | 8/1991 | Gold et al. |
| 5,048,970 A | 9/1991 | Milosevic et al. |
| 5,076,696 A | 12/1991 | Cohn et al. |
| 5,091,320 A | 2/1992 | Aspnes et al. |
| 5,096,298 A | 3/1992 | Isobe |
| 5,159,412 A | 10/1992 | Willenborg et al. |
| 5,166,752 A | 11/1992 | Spanier et al. |
| 5,181,080 A | 1/1993 | Fanton et al. |
| 5,189,481 A | 2/1993 | Jann et al. |
| 5,208,451 A | 5/1993 | Deck |
| 5,237,167 A | 8/1993 | Hibbard |
| 5,241,366 A | 8/1993 | Bevis et al. |
| 5,251,007 A | 10/1993 | Rinke |
| 5,262,845 A | 11/1993 | Milosevic et al. |
| 5,294,289 A | 3/1994 | Heinz et al. |
| 5,307,210 A | 4/1994 | MacFarlane et al. |
| 5,329,357 A | 7/1994 | Bermoux et al. |
| 5,333,052 A | 7/1994 | Finarov |
| 5,406,082 A | 4/1995 | Pearson et al. |
| 5,412,473 A | 5/1995 | Rosencwaig et al. |
| 5,450,201 A | 9/1995 | Katzir et al. |
| 5,451,369 A * | 9/1995 | Daeschel et al. ............ 422/28 |
| 5,483,347 A | 1/1996 | Hollmann |
| 5,485,271 A | 1/1996 | Drevillon et al. |
| 5,486,701 A | 1/1996 | Norton et al. |
| 5,517,032 A | 5/1996 | Imani |
| 5,517,312 A | 5/1996 | Finarov |
| 5,541,413 A | 7/1996 | Pearson et al. |
| 5,595,916 A | 1/1997 | Fujimura et al. |
| 5,596,406 A | 1/1997 | Rosencwaig et al. |
| 5,608,526 A | 3/1997 | Piwonka-Corle et al. |
| 5,627,671 A | 5/1997 | Yamura et al. |
| 5,764,365 A | 6/1998 | Finarov |
| 5,798,837 A | 8/1998 | Aspnes et al. |
| 5,910,842 A | 6/1999 | Piwonka-Corle et al. |
| 5,973,787 A | 10/1999 | Aspnes et al. |
| 5,978,074 A | 11/1999 | Opsal et al. |

FOREIGN PATENT DOCUMENTS

| | | |
|---|---|---|
| JP | 63-500263 | 1/1988 |
| JP | 63-32338 | 2/1988 |
| JP | 63-243836 | 10/1988 |
| JP | 1132935 | 5/1989 |
| JP | 1132936 | 5/1989 |
| JP | 214057 | 1/1990 |
| JP | 2126106 | 5/1990 |
| JP | 2297008 | 7/1990 |
| JP | 2118247 | 9/1990 |
| JP | 378645 | 4/1991 |
| JP | 4340404 | 11/1992 |
| JP | 5264355 | 10/1993 |
| JP | 5296841 | 11/1993 |
| JP | 6341952 | 12/1994 |
| JP | 7198342 | 8/1995 |
| JP | 8500432 | 1/1996 |
| SU | 947641 | 6/1980 |
| SU | 987410 | 5/1981 |
| SU | 11-60810 A1 | 4/1983 |
| SU | 12-88558 A1 | 4/1983 |
| SU | 11-40009 A | 7/1983 |
| SU | 11-41297 A | 10/1983 |
| SU | 11-57416 A | 12/1983 |
| SU | 12-60697 A1 | 7/1984 |
| SU | 13-69471 A | 2/1986 |
| SU | 13-37860 A1 | 9/1987 |
| SU | 15-71419 A1 | 12/1987 |
| SU | 16-95145 A1 | 8/1988 |

OTHER PUBLICATIONS

"A Mechanistic Study of Nitromethane Decomposition on Nickel," J.B. Benziger, *Application of Surface Science,* vol. 17, 1984, pp. 309–323.

"Characterization of Platinum Electrodes by Infrared Spectroscopy," J.B. Benziger et al., *J. Electroanal Chem.,* vol. 198, 1986, pp. 65–80.

"Considerations in building a low–noise reflection absorption infrared spectrometer," J.B. Benziger et al., *Applied Optics,* vol. 26, No. 2, Jan. 15, 1987, pp. 343–350.

"The Catalytic Chemistry of Hydrodesulfurization," R.E. Preston, Thesis 'in partial fulfillment' for Ph.D. submitted to Princeton University, 1984, pp. 1–208.

"Reactions to Organonitrogen Molecules with N1(100)," G.R. Schoofs et al., *J. Phys. Chem.,* vol. 92, No. 3, 1998, pp. 741–750.

"Reactions of Organonitrogen Molecules with Nickel(100)," G.R. Schoofs, Ph.D. Dissertation to Princeton University, 1986, pp. 1–261.

"Spatially resolved ellipsometry," M. Erman et al., *J. Appl. Phys.,* vol. 60, No. 3, Aug. 1, 1986, pp. 859–873.

"Angular scanning mechanism for ellipsometers," D.M. Byrne et al., *Applied Optics,* vol. 30, No. 31, Nov. 1, 1991, pp. 4471–4473.

"Ultraviolet–Visible Microspectrophotometer System for Small–Spot Measurement and Characterization of Thin Films," V.J. Coates et al., *Proceedings of SPIE—The International Society for Optical Engineering, Integrated Circuit Metrology, Inspection, and Process Control IV,* vol. 1261, Mar. 1990, pp. 492–494.

"Extension of spectroscopic ellipsometry to the far infrared," G. Dittmar et al., *Thin Solid Films,* vol. 234, Nos. 1–2, 1993, pp. 346–351.

"Far–infrared ellipsometer," K.L. Barth et al., *Rev. Sci. Instrum.,* 64(4), Apr. 1993, pp. 870–875.

"Infrared Spectroscopy of Oxide Layers on Technical Si Wafers," P. Grosse et al., *Appl. Phys. A,* vol. 39, 1986, pp. 257–268.

"Phase–modulated ellipsometer using a Fourier transform infrared spectrometer for real time applications," A. Canillas et al., *Rev. Sci. Instrum,* vol. 64, No. 8, Aug. 1993, pp. 2153–2159.

"In situ spectral ellipsometry for real–time thickness measurement: Etching multilayer stacks," S. Henck et al., *J. Vac. Sci. Technol. A,* vol. 11, No. 4, Jul./Aug. 1993, pp. 1179–1185.

"In situ spectral ellipsometer for real–time measurement and control," W.M. Duncan et al., *Applied Surface Science,* vol. 63, 1993, pp. 9–16.

"Problem of polarization degree in spectroscopic photometric ellipsometry (polarimetry)," A. Röseler, *J. Opt. Soc. Am. A,* vol. 9, No. 7, Jul. 1992, pp. 1124–1131.

"A reflectance anisotropy spectrometer for real–time measurements," O. Archer et al., *Rev. Sci. Instrum,* 63(11), Nov. 1992, pp. 5332–5339.

"Fast polarization modulated ellipsometer using a microprocessor system for digital Fourier analysis," B. Drevillon et al., *Rev. Sci. Instrum.,* vol. 53, No. 7, Jul. 1982, pp. 969–977.

"Spectroscopic ellipsometry under external excitation," G. Jin et al., *Thin Solid Films,* vol. 234, 1993, pp. 375–379.

"Orientation of Hydroquinone and Benzoquinone Adsorbed on Platinum Electrodes: Studies by Reflection–Absorption Infrared Spectroscopy," K.P. Pang et al., *J. Phys. Chem.,* vol. 88, No. 20, 1984, pp. 4583–4586.

"Spectroscopic Ellipsometry with High Lateral Resolution . . . ," M.M. Ehrman, These de Doctorat D'Etat, Dec. 1986, 352 pages.

"A reflectance anisotropy spectrometer for real time crystal growth investigations," O. Archer et al., *SPIE,* vol. 1361, 1990, pp. 1156–1163.

"Far–IR spectroscopic ellipsometer," K.–L. Barth et al., *Thin Solid Films,* vol. 234, 1993, pp. 314–317.

"Optical Constants of Materials in the Infra–red—Experimental Methods," J.R. Beattie, *The Philosophical Magazine,* vol. XLVI—$7^{th}$ Series, Jan.–Dec. 1955, pp. 235–245.

"Reactions of Organic Molecules on Transition Metal Surfaces," J.B. Benziger, Department of Chemical Engineering, Princeton University, Princeton, New Jersey, Final Report submitted to Air Force Office of Scientific Research, Report No.: AFOSR–TR–86–0148, Feb. 1986, 12 pages.

"Apparatus for the Study of Silicon Film Deposition and Silicon Etching," J.B. Benziger, Department of Chemical Engineering, Princeton University, Princeton, New Jersey, Final Report Submitted to Air Force Office of Scientific Research, Report No.: AFOSR–TR–87–1588, Jul. 31, 1987, 3 pages.

"Surface Intermediates in Thin Film Deposition of Silicon," J.B. Benziger, Department of Chemical Engineering, Princeton University, Princeton, New Jersey, Final Report Submitted to Air Force Office of Scientific Reseach, Report No.: AFOSR–TR–89–1754, Aug. 28, 1989, 13 pages.

"The Isosteric Phase Transformation of the Ni(100)–c(5√2× √2)R45° CO Surface," J.B. Benziger et al., *Surface Science,* vol. 171 (1986), pp. L401–L408.

"Adsorbate–Induced Reconstruction of p(2×2)X Adlayers On Ni(100)," J. Benziger et al., *Langmuir,* vol. 4, No. 2, 1988, pp. 268–276.

"Infrared phase modulated ellipsometer for in situ characterization of surfaces and thin films," N. Blayo et al., *Proceedings of SPIE—The International Society for Optical Engineering, Optically Based Methods for Process Analysis,* vol. 1681, 1992, pp. 116–127.

"On Tunneling Through An Intermediate (17–30A) Oxide Film In Silicon SiOSi Structures," S.K. Boitsov et al., *Russian Microelectronics,* vol. 22, No. 5, 1993, pp. 283–289 (originally published in Russian in *Mikroèlektronika,* Sep. 1993–Oct. 1993, pp. 74–82).

"IR Reflection–Absorption Spectroscopy of CO Adsorbed on Palladium," A.M. Bradshaw et al., *Surface Science,* vol. 52, 1975, pp. 449–454.

"An Ellipsometry System for High Accuracy Metrology of Thin Films," G.A. Candela et al., *Proceedings of SPIE—The International Society for Optical Engineering, Integrated Circuit Metrology II,* vol. 480, 1984, pp. 2–8.

"An IR phase–modulated ellipsometer using a Fourier transform spectrometer for in situ applications," A. Canillas et al., *Thin Solid Films,* vol. 234, 1993, pp. 318–322.

"Role of metal additives in light scattering from flame particles," T.T. Charalampopoulos et al., *Applied Optics,* vol. 31, No. 3, Oct. 20, 1992, pp. 6519–6528.

"High–temperature ellipsometer system to determine the optical properties of materials," T.T. Charalampopoulos et al., *Applied Optics,* vol. 33, No. 10, Apr. 1, 1994, pp. 1930–1937.

"Complete measurement of Kerr parameters by using rotating analyzer magneto–optic spectroscopy," L–Y. Chen et al., *Proceedings of SPIE—The International Society for Optical Engineering, Polarization Analysis and Measurement,* vol. 1746, 1992, pp. 307–315.

"Measurements of linear diattenuation and linear retardance spectra with a rotating sample spectropolarimeter," D.B. Chenault et al., *Applied Optics,* vol. 32, No. 19, Jul. 1, 1993, pp. 3513–3519.

"A broadband UV small spot spectroscopic ellipsometer," T.R. Corle et al., *Proceedings of SPIE—The International Society for Optical Engineering, Integrated Circuit Metrology, Inspection, and Process Control IX,* vol. 2439, Feb. 1995, pp. 114–125.

"A double polarization modulation far–infrared spectrometer," V.M. Da Costa et al., *Rev. Sci. Instrum.,* vol. 61, No. 8, Aug. 1990, pp. 2113–2120.

"Infrared Ellipsometric Spectroscopy of Adsorbed Species," M.J. Dignam et al., *Applied Spectroscopy Reviews,* vol. 14, No. 2, 1978, pp. 249–285.

"Design of a New In Situ Spectroscopic Phase Modulated Ellipsometer," B. Drevillon et al., *Proceedings of the SPIE—The International Society of Optical Engineering, Multichamber and In–Situ Processing of Electronic Materials,* vol. 1188, 1989, pp. 174–184.

"Rapid Scan Spectral Ellipsometry for In Situ Real–Time Wafer State Monitoring," W.M. Duncan et al., *The Electrochemical Society Proceedings,* vol. 94–33, pp. 193–206.

"High–speed spectral ellipsometry for in situ diagnostics and process control," W.M. Duncan et al., *J. Vac. Sci. Technol. B,* vol. 12, No. 4, Jul./Aug. 1994, pp. 2779–2784.

"Measuring films on and below polycrystalline silicon using reflectometry," H. Engstrom et al., *Proceedings of SPIE—The International Society of Optical Engineering, Integrated Circuit Metrology, Inspection, and Process Control V,* vol. 1464, Mar. 1991, pp. 566–573.

"Interface analysis by spectroscopic ellipsometry of $Ga_{1-x}Al_xAs$–GaAs heterojunctions grown by metal organic vapor phase epitaxy," M. Erman et al., *Appl. Phys. Lett.,* vol. 43, No. 3, Aug. 1, 1983, pp. 285–287.

"Spectroscopic ellipsometry study of InP, GaInAs, and GaIn As/InP heterostructures," M. Erman et al., *J. Appl. Phys.,* vol. 59, No. 6, Mar. 15, 1986, pp. 2019–2025.

"Electronic states and thicknesses of GaAs/GaAlAs quantum wells as measured by electroreflectance and spectroscopic ellipsometry," M. Erman et al., *I. Appl. Phy.,* vol. 56, No. 11, Dec. 1, 1984, pp. 3241–3249.

"A combined spectroscopic ellipsometer and spectrophotometer," J.J. Estabil et al., *Solid State Technology,* vol. 38, No. 4, Apr. 1995, pp. 71–72.

"Applications of IR Ellipsometric Spectroscopy to Surface Studies," J.D. Fedyk et al., *Surface Science,* vol. 89, 1879, pp. 404–424.

"Infrared spectroscopic ellipsometry using a Fourier transform infrared spectrometer: Some applications in thin–film characterization," F. Ferieu, *Rev. Sci. Instrum.*, vol. 60, No. 10, Oct. 1989, pp. 3212–3216.

"Characterization of the accretion of material by microparticles using resonant ellipsometry," L.M. Folan, *Applied Optics*, vol. 31, No. 12, Apr. 20, 1992, pp. 2066–2071.

"Application of the polarization modulation Fourier transform infrared spectroscopy for the in situ study of spontaneously adsorbed monolayers," M. Gatin et al., *Vibrational Spectroscopy*, vol. 5, 1993, pp. 255–261.

"Chemical and Structural Analysis by Ellipsometry and X–Ray Reflectometry of Thin Sulfide Layers Grown on InP," M. Gendry et al., *Applied Surface Science*, vol. 44, 1990, pp. 309–320.

"A Method for Measuring Infrared Reflection–Absorption Spectra of Molecules Adsorbed on Low–Area Surfaces at Monolayer and Submonolayer Concentrations," W.G. Golden et al., *Journal of Catalysis*, vol. 71, 1981, pp. 395–404.

"Infrared Reflection–Absorption Spectroscopy of Surface Species: A Comparison of Fourier Transform and Dispersion Methods," W.G. Golden et al., *J. Phys. Chem.*, vol. 88, No. 3, 1984, pp. 574–580.

"Infrared Spectropolarimetry," D.H. Goldstein et al., *Optical Engineering*, vol. 28, No. 2, Feb. 1898, pp. 120–125.

"Broadband spectroscopic ellipsometry based on a Fourier transform spectrometer," A. Gombert et al., *Thin Solid Films*, vol. 234, 1993, pp. 352–355.

"Quantitative infrared spectroscopy of thin solid and liquid films under attenuated total reflection conditions," P. Grosse et al., *Vibrational Spectroscopy*, vol. 8, 1995, pp. 121–133.

"VII—Multi–Purpose Reflection The Seagull™," Harrick Scientific Corporation, from website address http://www.harricksci.com//products/page34.hl. 3 pages.

"Automated spatially scanning ellipsometer for retardation measurements of transparent materials," J.E. Hayden et al., *Applied Optics*, vol. 32, No. 31, Nov. 1, 1993, pp. 6256–6263.

"Infrared Reflection–Absorption Spectroscopy of Adsorbed Molecules," F.M. Hoffmann, *Surface Science Reports*, vol. 3, 1983, pp. 107–192.

Mid– and near–IR ellipsometry of $Y_{1-x}Pr_xPr_xBa_2Cu_3O_7$ epitaxial films, J. Humlicek et al., *Thin Solid Films*, vol. 234, 1993, pp. 518–521.

"Reflectance–difference spectroscopy of (001) GaAs surfaces in ultrahigh vacuum," I Kamiya et al., *Physical review B*, vol. 46, No. 24, Dec. 15, 1992, pp. 15 894–15 904.

"Ultrathin Layers of Titanium Oxide on Silicon Surface: An Ellipsometric Study of Matching between Two Structures," S.I. Kol'tsov et al., *Phys. Chem Mech. Surfaces*, vol. 8, No. 5, 1993, pp. 714–721.

"In situ infrared reflection absorption spectroscopic characterization of plasma enhanced chemical vapor deposited on $SiO_2$ films," K.B. Koller et al., *J. Appl. Phys.*, vol. 64, No. 9, Nov. 1, 1988, pp. 4704–4710.

"Ellipsometric tomography," V.A. Kotenev, *Proceedings of SPIE—The International Society for Optical Engineering, Analytical Methods for Optical Tomography*, vol. 1843, Nov. 1991, pp. 259–269.

"Infrared Ellipsometry on Silicon Wafers," T.A. Leonard et al., *Proceedings of SPIE—The International Society of Optical Engineering, Integrated Circuit Metrology II*, vol. 480, 1984, pp. 9–13.

"Design and construction of three infrared ellipsometers," T.A. Leonard et al., *Optical Engineering*, vol. 21, No. 6, Dec. 1982, pp. 971–975.

"Investigation of Optical Surfaces with a New, Automated Ellipsometer Arrangement," M. Linder, *Proceedings ECO1, In–Process Optical Measurements*, vol. 1012, Sep. 1998, p. 47–50.

"Two–wavelength infrared interferometer/polarimeter system for CIT," C.H. Ma et al., *Rev. Sci. Instrum.*, vol. 59, No. 8, Aug. 1988, pp. 1629–1631.

"Limits of laser scattering defect inspection tools on patterned wafers," H. Martin et al., *SPIE—The International Society for Optical Engineering, Integrated Circuit Metrology, Inspection, and Process Control VIII*, vol. 2196, Feb.–Mar. 1994, pp. 200–210.

"Optical In–Situ Methods of High Local Resolution for the Investigation of Corrosion Processes," A. Michaelis et al., *An International Journal of Berichte Der Bunsen–Gesellschaft*, vol. 97, No. 3, 1993, pp. 431–435.

"Applications of the Theory of Optical Spectroscopy to Numerical Simulations," M. Milosevic et al., *Applied Spectroscopy*, vol. 47, No. 5, 1993, pp. 566–574.

"The Seagull®: A Multifunctional Variable–Angle Reflection Attachment," M. Milosevic et al., *Applied Spectroscopy*, vol. 45, No. 1, 1991, pp. 126–131.

"Experimental aspects of attenuated total reflectance spectroscopy in the infrared," V. Offermann et al., *Vibrational Spectroscopy*, vol. 8, 1995, pp. 135–140.

"In situ investigation by IR ellipsometry of the growth and interfaces of amorphous silicon and related materials," R. Ossikovski et al., *Thin Solid Films*, vol. 363–366.

"Anomalous behavior of density and mechanical properties of thermosetting polymers with increasing conversion," K.P. Pang, Ph.D. Dissertation, Jan. 1989, pp. 1–203.

"Orientation of Hydroquinone and P–Benzoquinone adsorbed on Platinum Electrodes: Studies by Reflection–Absorption Infrared Spectroscopy," K.P. Pang, A Thesis Submitted 'in partial fulfillment' for Ph.D. to Department of Engineering, Princeton University, Jun. 1984, pp. 1–50.

"The fastest real time spectroscopic ellipsometry: applications and limitations for in situ and quality control," J.–P. Piel et al., *Thin Solid Films*, vol. 233, 1993, pp. 301–306.

"Accuracy of Determining Optical Constants of Absorbing Substances by Reflection in an Arrangement Using a Polarizer and Analyzer," A.P. Prishivalko, *Optika II Spectroskopiya*, 10, 1961, pp. 131–135.

Sagax Instruments product brochure for the Sagax 225, dated 1980's.

"Differential Ellipsometry," T. Sandström, *Journal de Physique*, Conference No. C10, Supplement with No. 12, vol. 44, Dec. 1983, pp. C10–75–C10–78.

Sentech Instruments product brochure for the Infrared Spectroscopic Ellipsometer SE 900—FT–IR Ellipsometer for vibrational spectroscopy and metrology of thin films—undated.

"Profiles of Optical Constants of Inhomogeneous Layers Determined by Ellipsometric Measurements In Situ," V.A. Shvets, *Optoelectronics, Instrumentation and Data Processing (Avtometriya)*, No. 6, 1993, pp. 25–32.

"Double film thickness measurements in the semiconductor industry," R.F. Spanier, *Proceedings of SPIE—The International Society of Optical Engineering, Integrated Circuit Metrology*, vol. 342, May 1982, pp. 109–120.

"Sensitivity of the reflection technique: optimum angles of incidence to determine the optical properties of materials," B.J. Stagg et al., *Applied Optics,* vol. 31, No. 22, Aug. 1, 1992, pp. 4420–4427.

"Source–optics polarization effects on ellipsometry analysis," B.J. Stagg et al., *Applied Optics,* vol. 33, No. 16, Jun. 1, 1994, pp. 3493–3501.

"Method for azimuthal alignment in fixed–angle ellipsometry," B.J. Stagg et al., *Applied Optics,* vol. 31, No. 4, Feb. 1, 1992, pp. 479–484.

"Method to minimize the effects of polarizer leakage on reflectivity measurements," B.J. Stagg et al., *Applied Optics,* vol. 29, No. 31, Nov. 1, 1990, pp. 4638–4645.

"A New Micro Spectroscopic Ellipsometer for On Line Control in Silicon Industry Developed for Tencor Prometrix," J.L. Stehle et al., WISE '95 Workshop International on Spectroscopic Ellipsometry, Feb. 1995.

"Geometrical Resolution in the Comparison Ellipsometer," L. Stiblert et al., *Journal de Physique,* Conference C10, Supplement with No. 12, vol. 44, Dec. 1983, pp. C10–70–C10–82.

"Automatic Ellipsometer with High Sensitivity and Special Advantages of Infrared Spectroscopy of Adsorbed Species," R.W. Stobie et al.,*Applied Optics,* vol. 14, No. 4, Apr. 1975, pp. 999–1003.

"Extension of Ellipsometry to the Case of High–Reflectance Small Samples and Long–Wavelength Radiation," A.B. Sushkov et al., *Optics and Spectroscopy,* vol. 76, No. 3, Mar. 1994, pp. 407–413.

"Ellipsometric Investigation of Transition Layer Heterostructures," S.A. Titov et al., *Instruments and Experimental Techniques,* vol. 37, No. 4, Part 2, Jul.–Aug. 1994, pp. 475–478.

"Ultrasensitive thermal lens–circular cichroism spectropolarimeter for small–volume samples," C.D. Tran et al., *Rev. Sci. Instrum.,* vol. 60, No. 10, Oct. 1989, pp. 3207–3211.

Multichannel transmisson ellipsometer for characterization of anisotropic optical materials, R.A. Yarussi et al., *J. Opt. Soc. Am. A.,* vol. 11, No. 8, Aug. 1994, pp. 2320–2330.

"Measurement of Epitaxial Film Thickness Using an Infrared Ellipsometer," R.A. Hilton et al., *Journal of the Electrochemical Society,* vol. 113, No. 5, May 1966, pp. 472–478.

"Characterization of layer systems by means of spectroscopic ellipsometry in the far infrared," Dissertation by George Dittmar, from Rhein/Westfalie Technical University (RWTH) in Aachen, Jun. 1994 (English translation of introduction only).

"Anhang: Weitere 'dielectrische Funktionen," No author, publication name or publication date provided) (English translation of p. 143 only).

"Characterization of thin layers by means of quantitative ATR spectroscopy in the infrared," Dissertation by Volkmar Offermann, from Rhein/Westfalie—Technical University (RSTH) in Aachen, Jun. 2, 1995.

"Use of Ellipsometry to Measure the Thicknesses of Dielectric Films on Individual Elements of Integrated Circuits," A.P. Antsiferov et al., *Mikroelektronika,* vol. 4, No. 3, 1975, pp. 273–275 (English translation of p. 237 only).

"Mikroscan LEF–801 High–Spatial–Resolution Scanning Ellipsometer," A. Aul'chenko et al., *Pribory I Tekhnika Experimenta,* vol. 5, 1992, pp. 242–244 (English translation of pp. 242–243 only).

"Checking the Parameters of Epitaxial Structures by Infrared Ellipsometry," V.V. Batavin et al., *Elektronnaya Promyslennost',* vol. 5, No. 42 (1974), pp. 42–45 (English translation of p. 42 only).

"Automatic Ellipsometry System," M.I. Yelinson, *Eliktronnaya Promyshlennost',* No. 10–11, 1982, pp. 100–103 (English translation of p. 100 only).

"Contrast and Resolution of Ellipsometric Microscopy," Yu. A. Kontsevoi et al., *Zavodskaya Laboratoriya,* vol. 9, 1993, pp. 26–29 (English translation of p. 26 only).

"In Ellipsometry: theory, methods and applications," E.S. Lonskii (Nauka, Novasibirsk, 1991), pp. 138–147 (English translation of first paragraph ranging pages 138–139 only).

"Measurement of Thickness of Epitaxial Silicon Layers by Far–Infrared Ellipsometry," V.I. Mishnev et al., *Mikroelektronika,* vol. 1, No. 2, 1972, pp. 152–155 (English translation of p. 152 only).

*Principals of Ellipsometry,* A.V. Rzhanov et al., *Science,* 1979, pp. 1–425 (English translation of title page and Table of Contents only).

"Ellipsometric Studies of the Surface of Local Objects In a Focused Light Beam," Y.V. Spesivtsev et al., *In Ellipsometry: theory, methods and applications* (Nauka, Novosibirsk, 1994), pp. 84–89 (English translation of p. 84 only).

"Measurement of the Thickness of Epitaxial Semiconductor Films," K.K. Svitashev et al., *Mikroelektronika,* vol. 2, No. 5, 1973, pp. 454–460 (English translation of p. 455 only).

"Infrared–Ellipsometer Sighting Device for Local Measurements of Electrophysical Parameters of Semiconductor Structures," N.M. Zudkov et al., *Elektronnaya Tekhnika. Seriya Materialy,* No. 3, 1978, pp. 126–127 (English translation provided).

"Precision ellipsometry based on a focused light beam, Part 1," D.O. Barsukov et al., *Opt. Spectrosc..*(USSR), vol. 64, No. 6, Jun. 1988, pp. 782–785 (both English and Russian versions submitted).

"Precision ellipsometry based on a focused light beam, Part 2: Analysis of sensitivity," D.O. Barsukov et al., *Opt. Scpectrosc.* (USSR), vol. 65, No. 2, Aug. 1988 (both English and Russian versions submitted).

"Effect of light–beam convergence in an ellipsometer," A.I. Semenenko et al., *Sov. Tech. Phys. Lett.,* vol. 3, No. 12, Dec. 1977, pp. 538–540 (both English and Russian versions submitted).

"Ellipsometry of a convergent beam in the far infrared," A.B. Sushkov et al., *Opt. Spectrosc.* (USSR), vol. 72, No. 7, Feb. 1992, pp. 268 (both English and Russian versions submitted).

"Use of a Convergent Light Beam for Ellipsometric Measurements," K.K. Svitashev et al., *Optics and Spectroscopy,* 1971, pp. 532–538 (both English and Russian versions submitted).

"Ellipsometry based on a convergent light beam," K.K. Svitashev et al., *Opt. Spectrosc.,* vol. 34, No. 5, May 1973, pp. 542–544 (both English and Russian versions submitted).

"High Precision Scanning Ellipsometer," D.E. Aspnes et al., *Applied Optics,* vol. 14, No. 1, Jan. 1975, pp. 220–228.

"Spectroscopic ellipsometry: a new tool for "on line" quality control," D. Zahorski et al., *Thin Solid Films,* vol. 234, 1993, pp. 412–415.

"High–precision reflectometer for submillimeter wavelengths," A.J. Gatesman et al., *J. Opt. Soc. Am. B,* vol. 12, No. 2, Feb. 1995, pp. 212–219.

R.M.A. Azzam and N.M. Bashara, *Ellipsometry and Polarized Light,* North–Holland (1977, paperback ed. 1987), pp. 375–376.

Harold H. Bloem, William E. Goetz, Ralph N. Jackson, and Richard W. Kern, *Development of an Automatic Ellipsometer,* Electro–Optical Systems Design, Mar. 1980, pp. 38–45.

M. Erman and J.B. Theeten, *Spatially Resolved Ellipsometry,* J. Appl. Phys. 60, Aug. 1, 1986, pp. 859–873.

Y. Demay, J.P. Gailliard, and P. Medina, *In Situ Spectroscopic Ellipsometry of Mercury Cadmium Telluride MBE Layers,* Journal of Crystal Growth 81, 1987, pp. 97–100.

Dale M. Byrne and Duncan L. MacFarlane, *Angular Scanning Mechanism for Ellipsometers,* Applied Optics, vol. 30, No. 31, Nov. 1, 1991, pp. 4449 & 4471–4473.

* cited by examiner

EX PARTE REEXAMINATION CERTIFICATE ISSUED UNDER 35 U.S.C. 307

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

AS A RESULT OF REEXAMINATION, IT HAS BEEN DETERMINED THAT:

The patentability of claims 1–21 and 23–72 is confirmed.

Claim 22 is determined to be patentable as amended.

New claims 73–83 are added and determined to be patentable.

22. The ellipsometer of claim 18, wherein the autofocus assembly includes:
   camera means *observing a position of the spot*; and
   an apertured mirror positioned along the optical path between the all-reflective optics and analyzer, for reflecting said radiation reflected from a spot on the sample during movement of the sample stage means to the camera means.

*73. The ellipsometer of claim 1, wherein the detector detects substantially simultaneously multiple wavelengths in the output beam to provide a detected output; and the processing means processes the detected output to measure polarized radiation reflected from the sample at said multiple wavelengths.*

*74. The ellipsometer of claim 22, wherein the camera means provides a focus signal indicative of position of the spot from said portion of the sample beam, and*
   *the processing means generates from the focus signal focus control signals for focusing radiation to the sample.*

*75. The ellipsometer of claim 1, said detector comprising a UV-enhanced CCD array detector that measures intensity of said output beam at each of a number of different wavelength ranges.*

*76. The method of claim 25, wherein the detecting detects substantially simultaneously multiple wavelengths in the output beam to provide a detected output.*

*77. The instrument of claim 39, wherein the detector means detects substantially simultaneously multiple wavelengths in the output beam to provide a detected output.*

*78. The instrument of claim 39, said detector means comprising a UV-enhanced CCD array detector that measures intensity of said output beam at each of a number of different wavelength ranges.*

*79. The instrument of claim 44, wherein the detector means detects substantially simultaneously multiple wavelengths in the output beam to provide a detected output.*

*80. The instrument of claim 44, said detector means comprising a UV-enhanced CCD array detector that measures intensity of said output beam at each of a number of different wavelength ranges.*

*81. The ellipsometer of claim 50, wherein the detector means detects substantially simultaneously multiple wavelengths in the output beam to provide a detected output.*

*82. The ellipsometer of claim 52, wherein the detector means detects substantially simultaneously multiple wavelengths in the output beam to provide a detected output.*

*83. The method of claim 66, wherein the detecting detects substantially simultaneously multiple wavelengths in the output beam to provide a detected output.*

* * * * *